US010881835B2

(12) United States Patent
De Zolt et al.

(10) Patent No.: US 10,881,835 B2
(45) Date of Patent: Jan. 5, 2021

(54) MEDICAL DEVICE WITH RESILIENTLY RETRACTING SAFETY NEEDLE

(71) Applicant: SOL-MILLENNIUM SWISS R&D CENTER SA, Lugano (CH)

(72) Inventors: Dario De Zolt, Fagnano Olona (IT); Matteo Lagana, Longone al Segrino (IT)

(73) Assignee: SOL-MILLENNIUM SWISS R&D CENTER SA, Lugano (CH)

( * ) Notice: Subject to any disclaimer, the term of this patent is extended or adjusted under 35 U.S.C. 154(b) by 0 days.

(21) Appl. No.: 16/613,703

(22) PCT Filed: Sep. 6, 2018

(86) PCT No.: PCT/IB2018/056808
§ 371 (c)(1),
(2) Date: Nov. 14, 2019

(87) PCT Pub. No.: WO2019/053568
PCT Pub. Date: Mar. 21, 2019

(65) Prior Publication Data
US 2020/0289792 A1    Sep. 17, 2020

(30) Foreign Application Priority Data
Sep. 14, 2017   (IT) .......................... 102017000103120

(51) Int. Cl.
*A61M 25/06*       (2006.01)
(52) U.S. Cl.
CPC .... *A61M 25/0631* (2013.01); *A61M 25/0637* (2013.01)

(58) Field of Classification Search
CPC .......... A61M 25/0631; A61M 25/0637; A61M 25/06; A61M 25/0606; A61M 25/0612;
(Continued)

(56) References Cited

U.S. PATENT DOCUMENTS 5,891,098 A * 4/1999 Huang .............. A61M 25/0631
                                                    128/919
2004/0267200 A1   12/2004 Carlyon et al.
(Continued)

FOREIGN PATENT DOCUMENTS

EP    1306097 A1    5/2003
EP    1520598 A2    4/2005
(Continued)

OTHER PUBLICATIONS

International Search Report and Written Opinion for Corresponding International Application No. PCT/IB2018/056808 (10 Pages) ( dated Dec. 19, 2018).

*Primary Examiner* — Kami A Bosworth
*Assistant Examiner* — Antarius S Daniel
(74) *Attorney, Agent, or Firm* — Lucas & Mercanti, LLP

(57) ABSTRACT

A medical device for percutaneous or venous access for the purposes of administering a fluid to a patient or sampling from one is disclosed. The device includes a cannula holder that has a part or portion of cross-section which is reduced or different from its distal end and proximal end. The part or portion of reduced or different cross-section allows the cannula holder to deform within the body of the device when activating means are activated to separate the cannula holder from an immobilising member allowing the cannula holder to move in the body of the device and re-enter and disappear within such body of the cannula.

16 Claims, 22 Drawing Sheets

(58) Field of Classification Search
CPC .... A61M 5/158; A61M 5/322; A61M 5/3232; A61M 5/321
See application file for complete search history.

(56) References Cited

U.S. PATENT DOCUMENTS

2009/0131872 A1* 5/2009 Popov ............... A61M 25/0625
604/164.08
2016/0008538 A1* 1/2016 Isaacson ............. A61M 5/1626
604/263

FOREIGN PATENT DOCUMENTS

WO           9924092 A1    5/1999
WO        2016007438 A1    1/2016

* cited by examiner

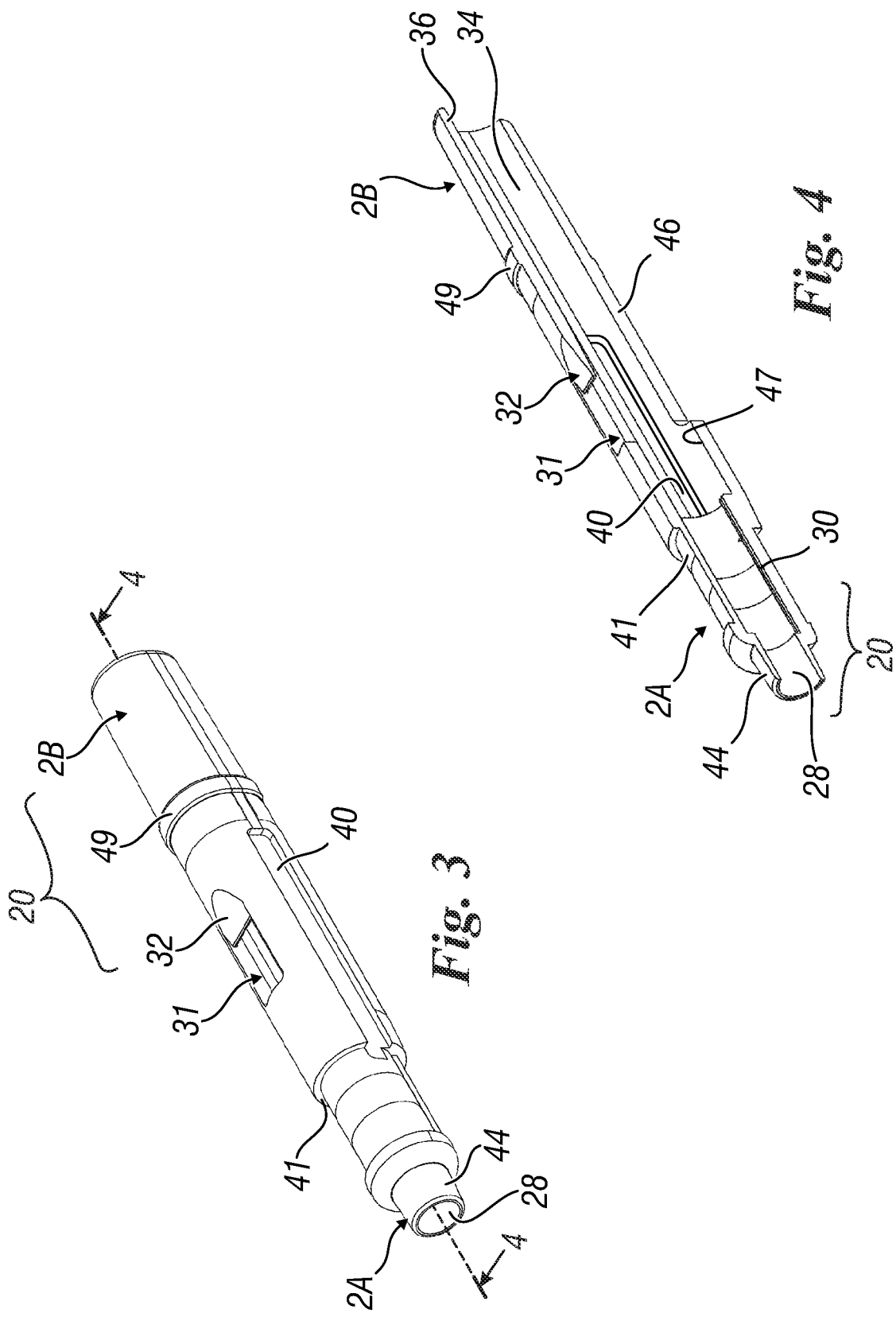

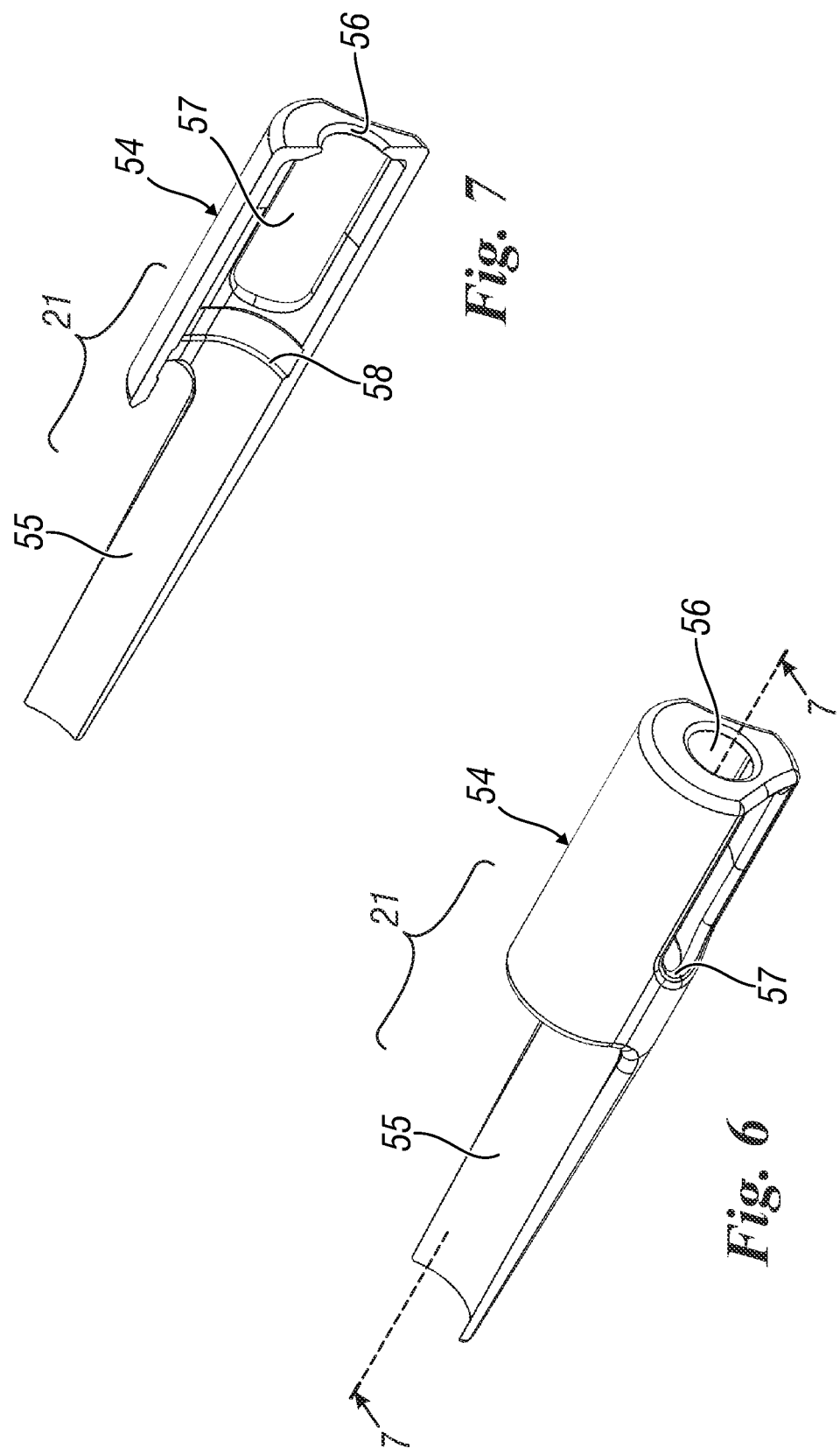

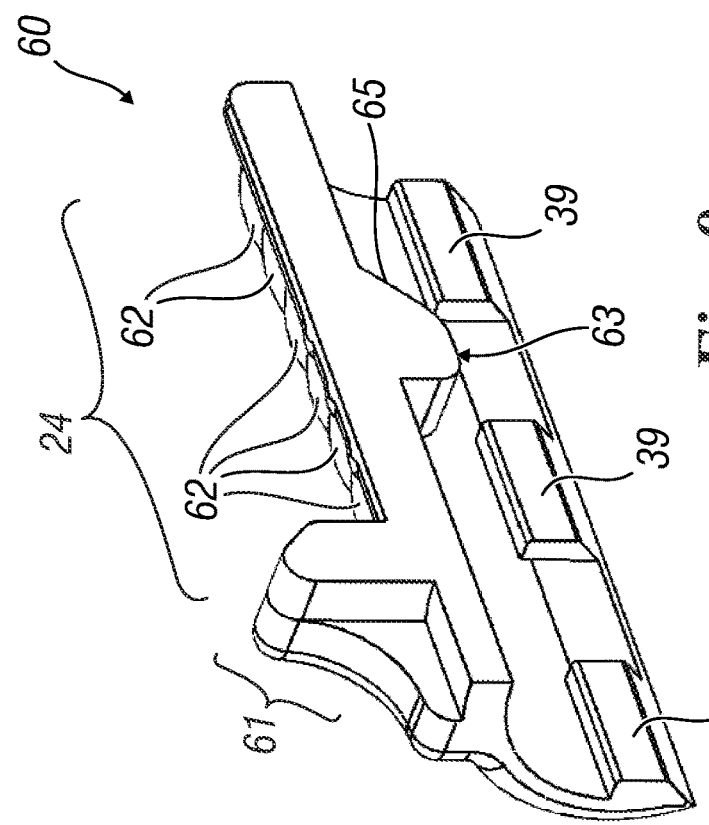
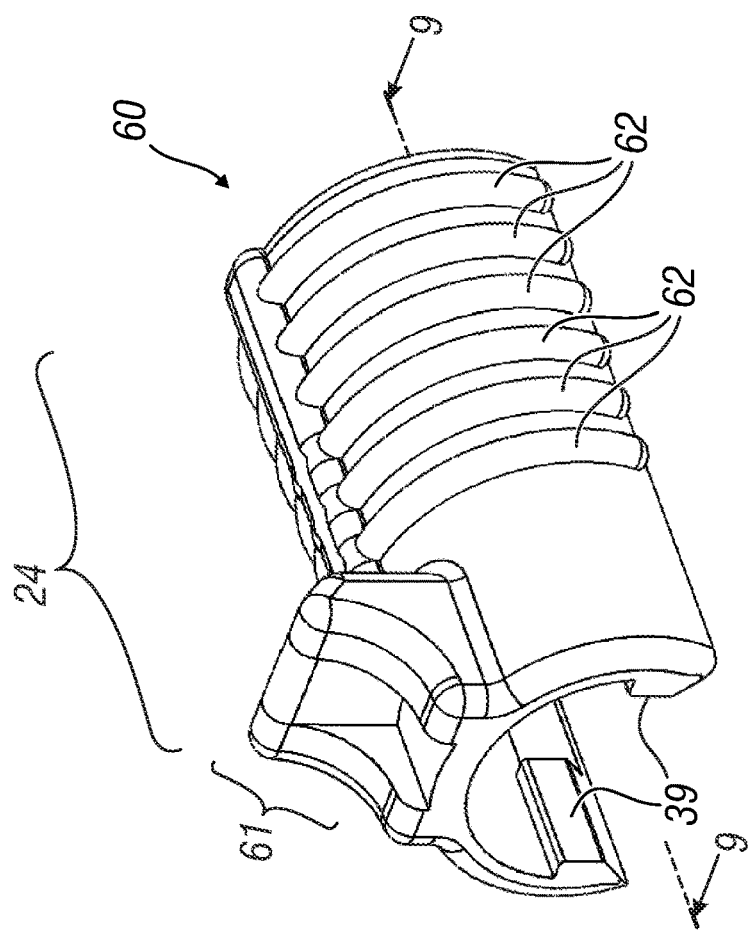

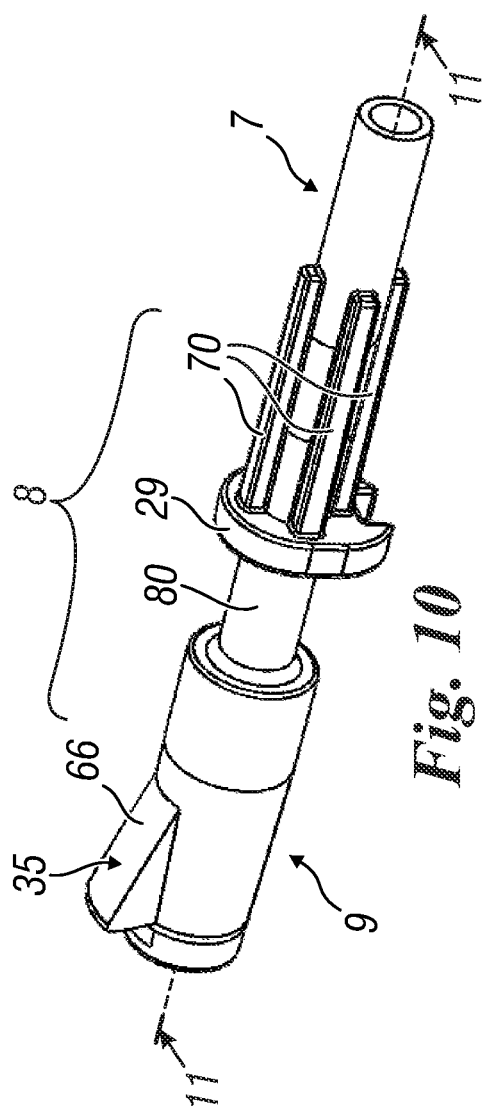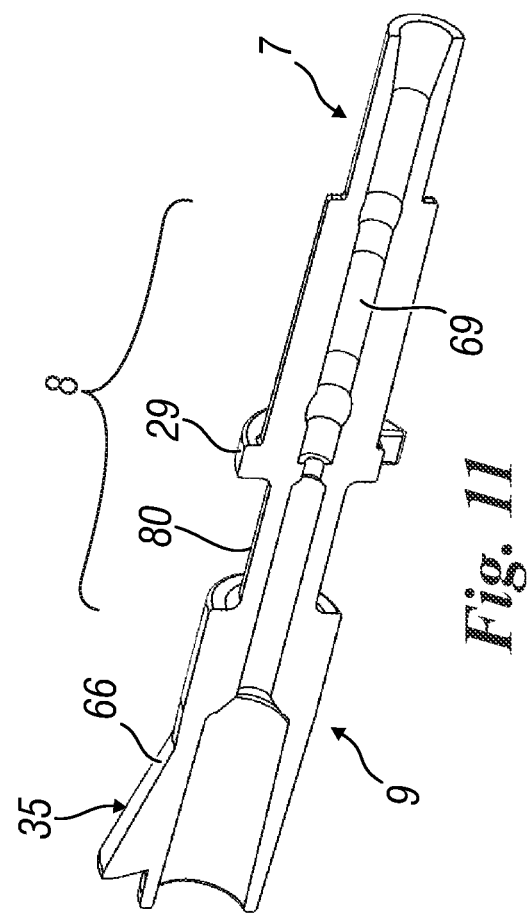

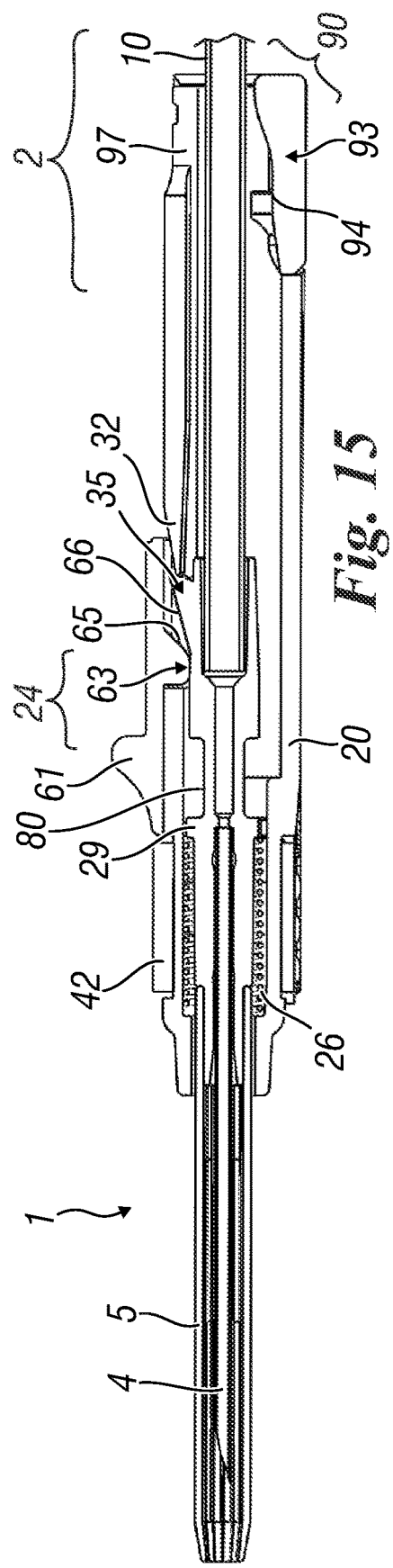
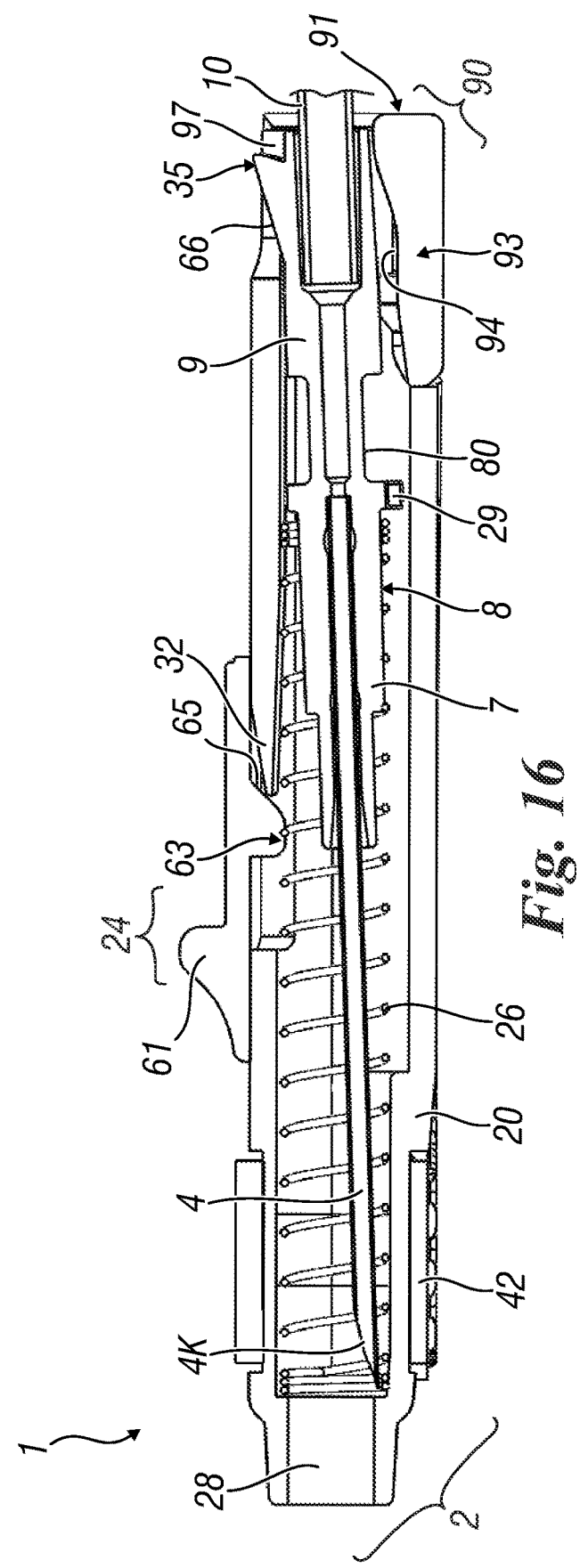

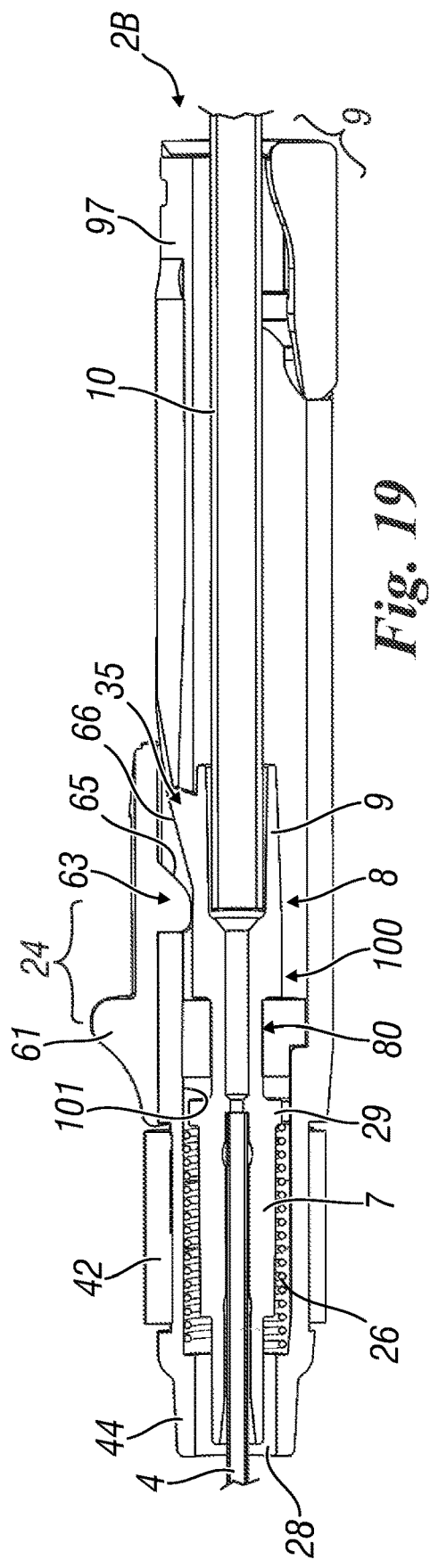
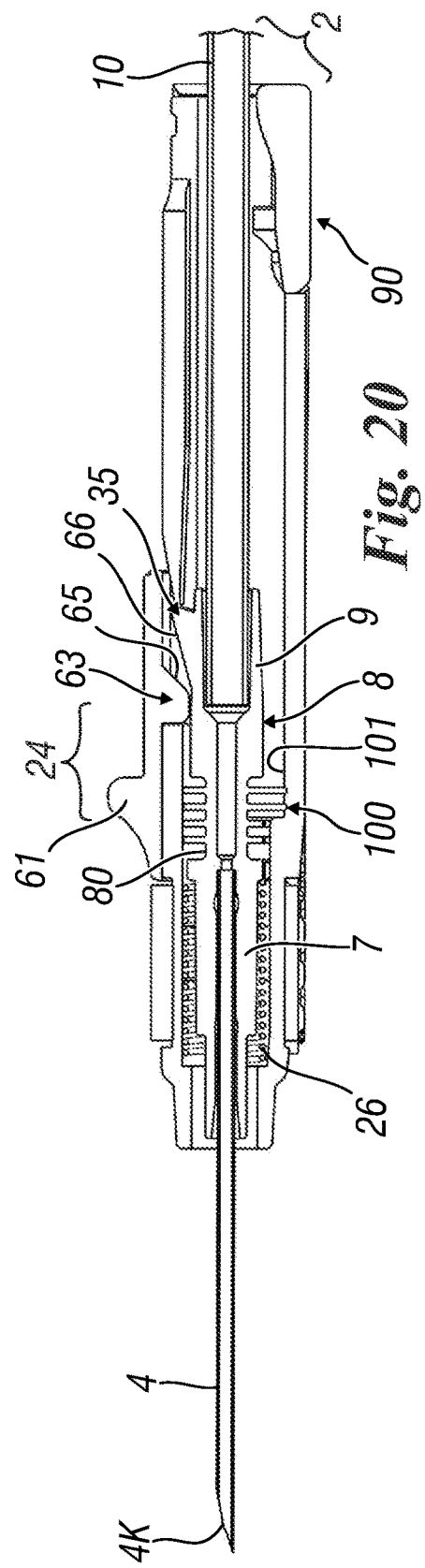
Fig. 19
Fig. 20

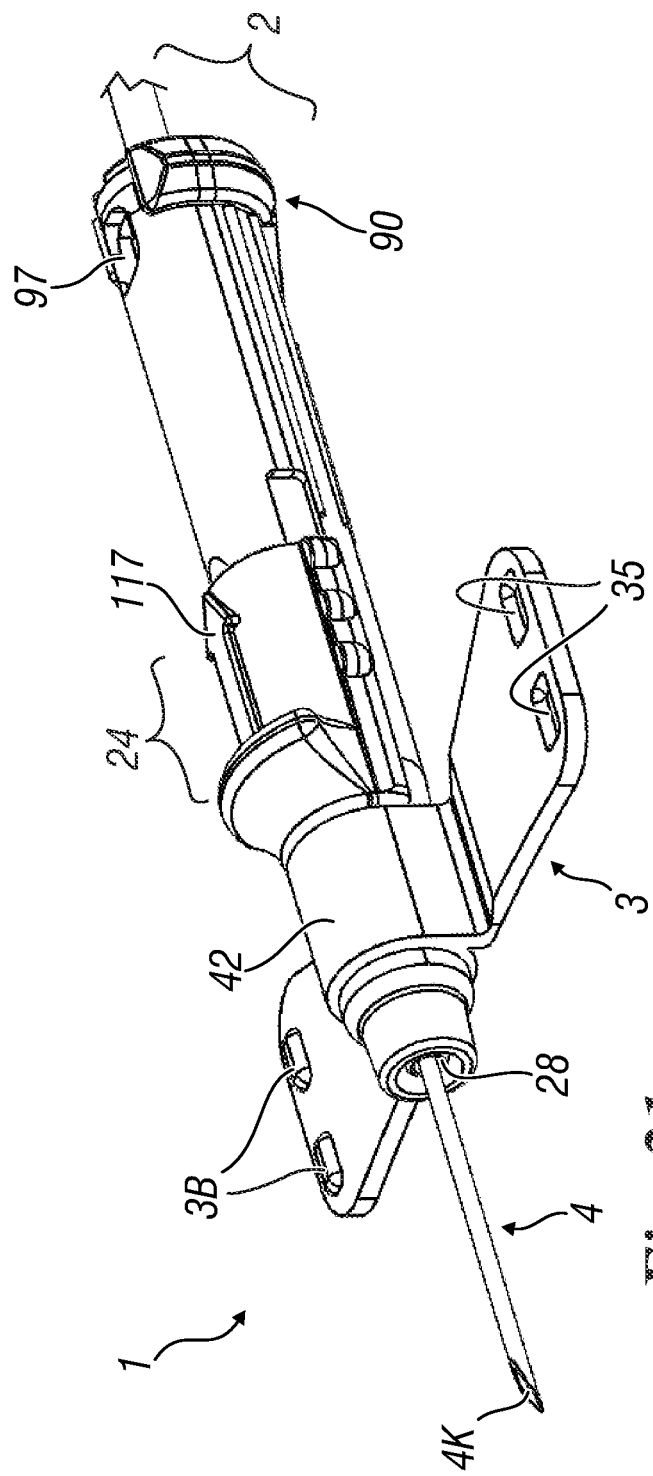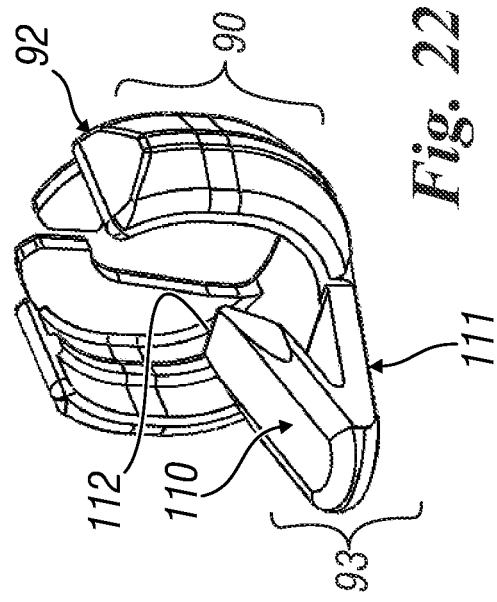

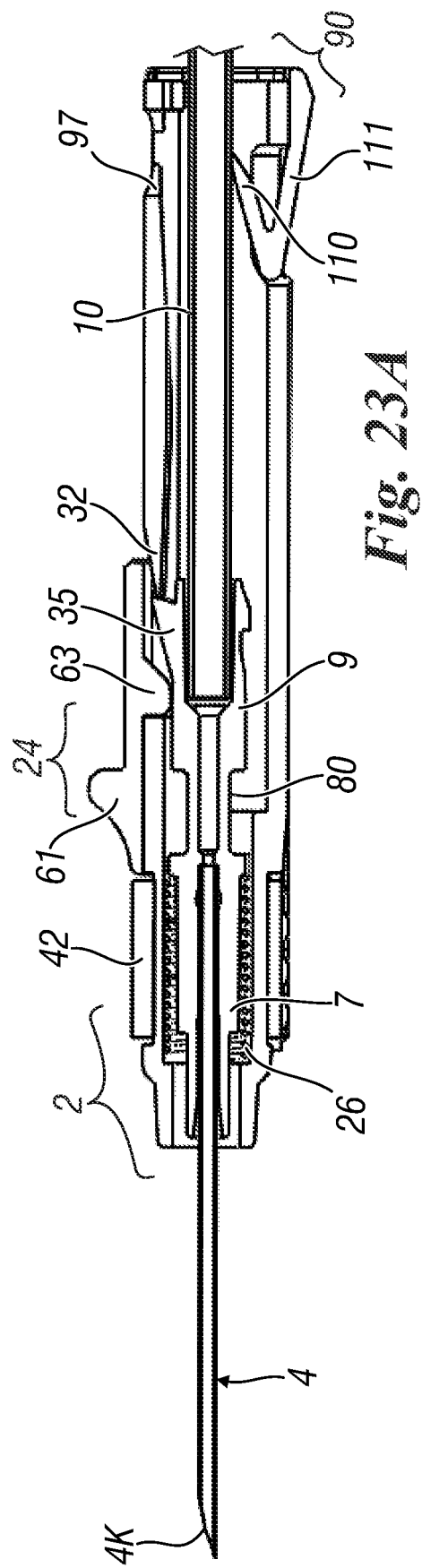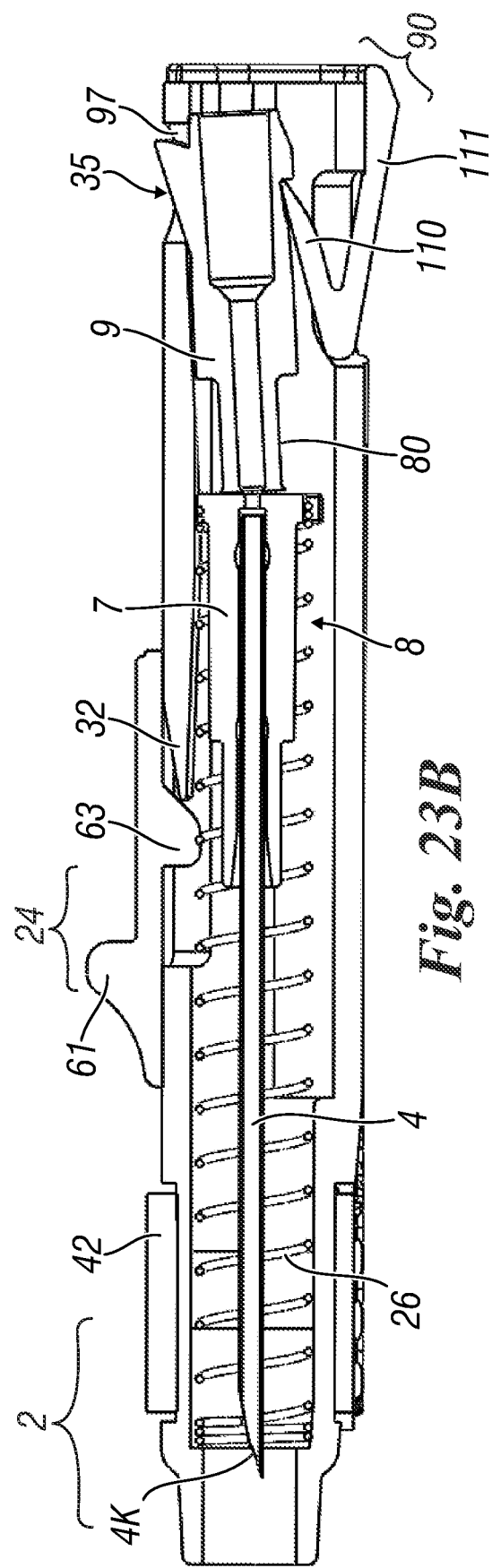

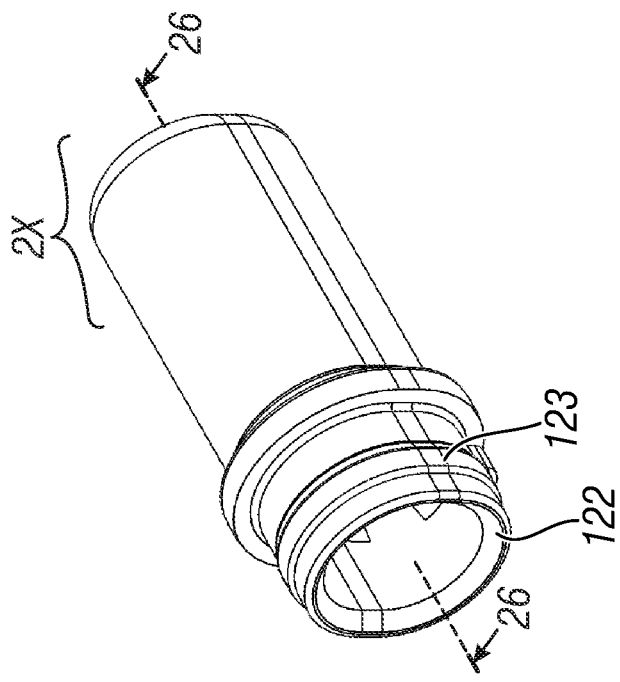
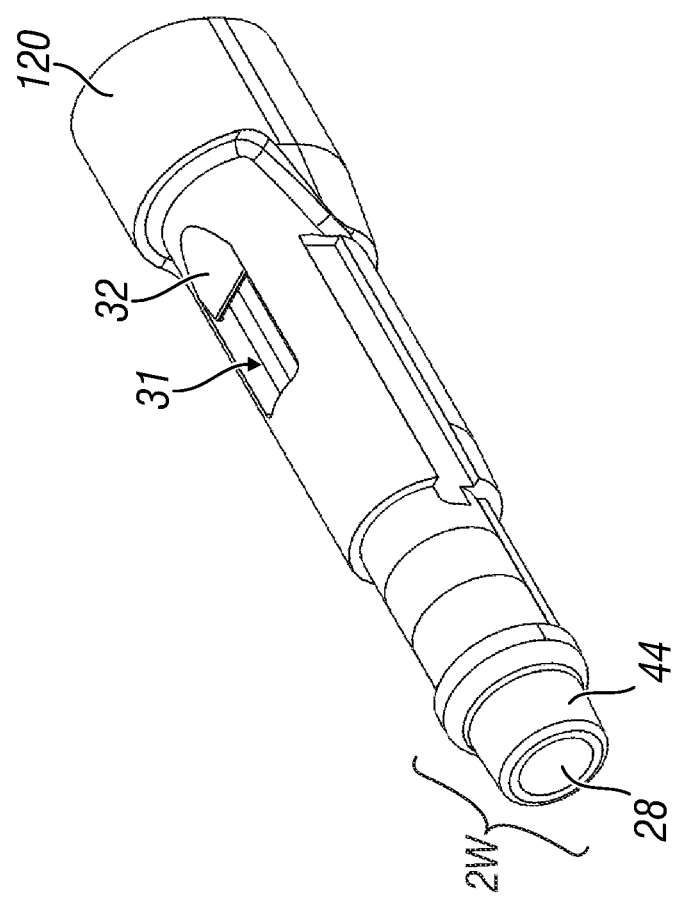
Fig. 25

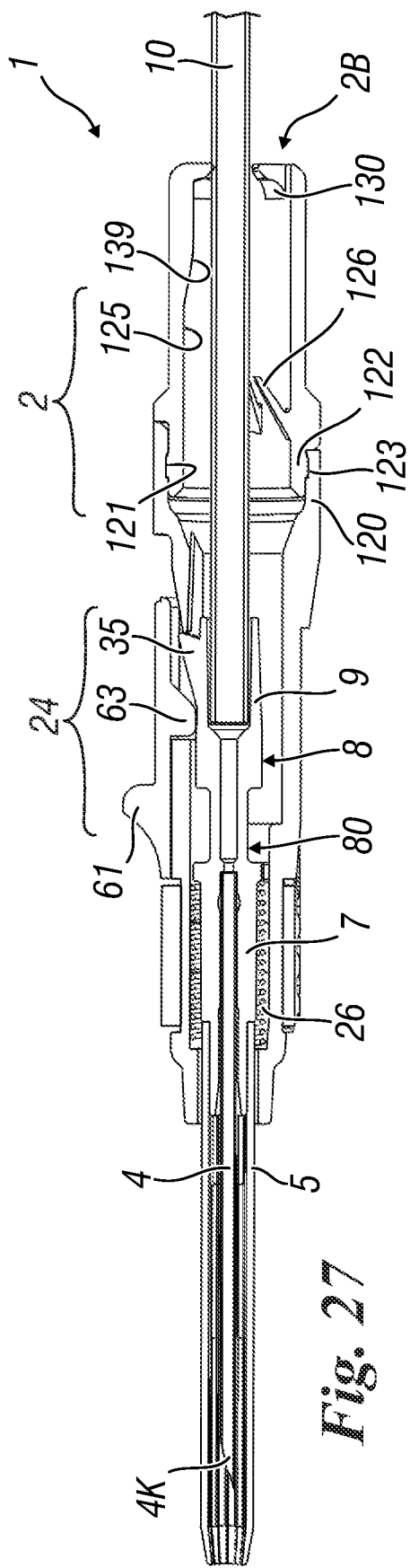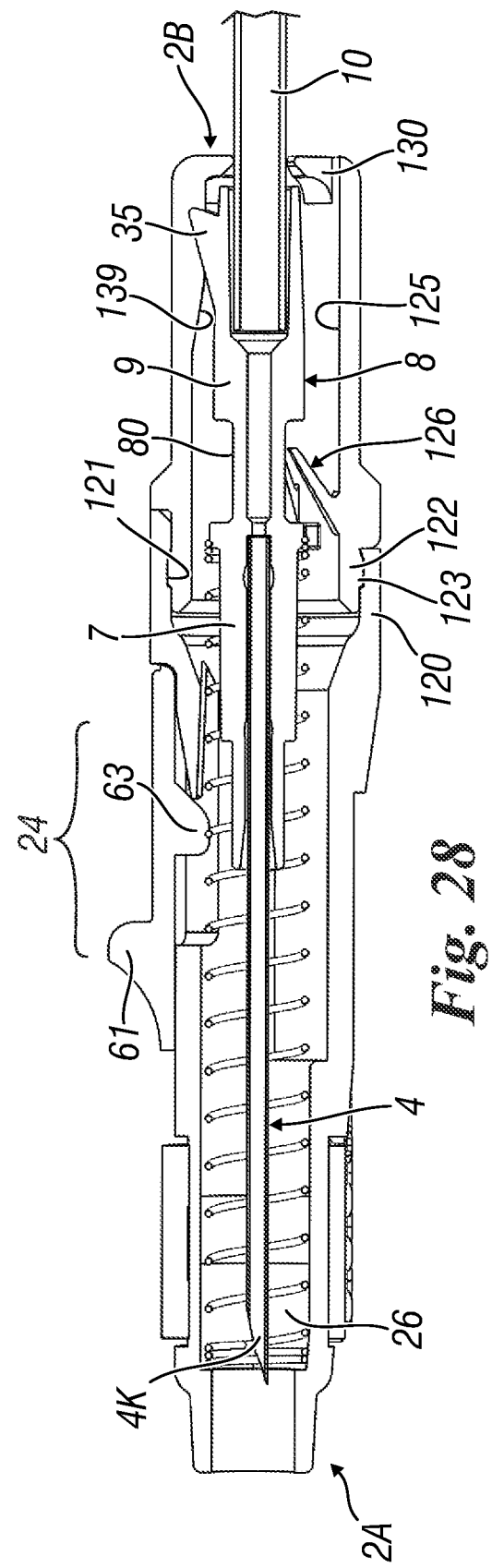

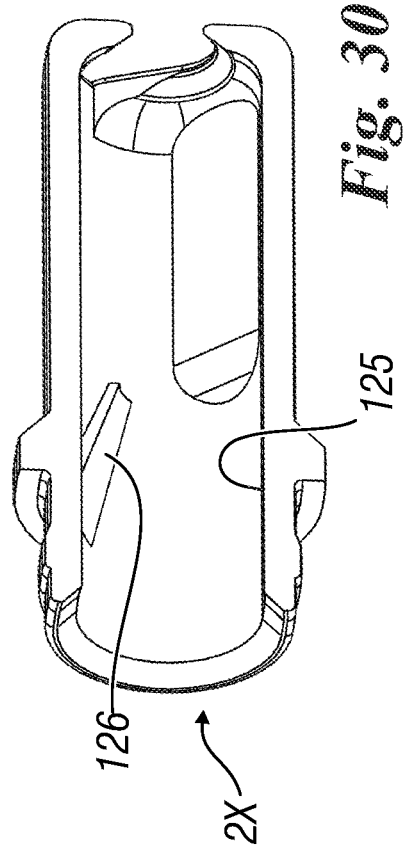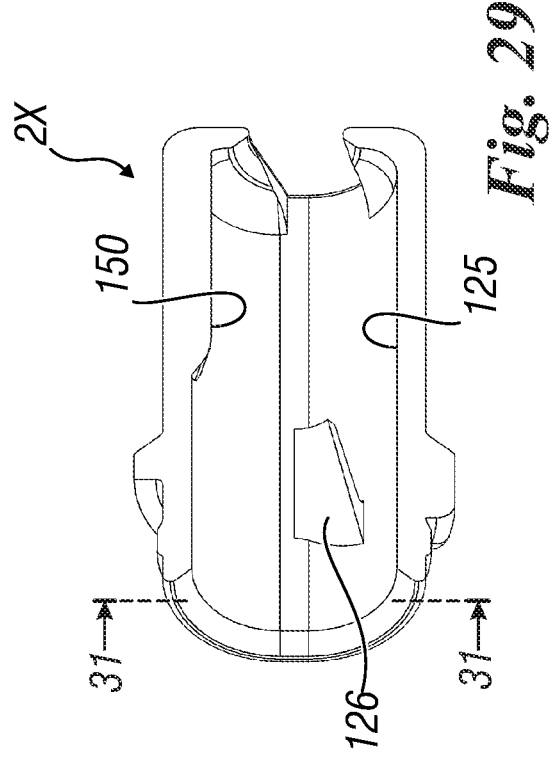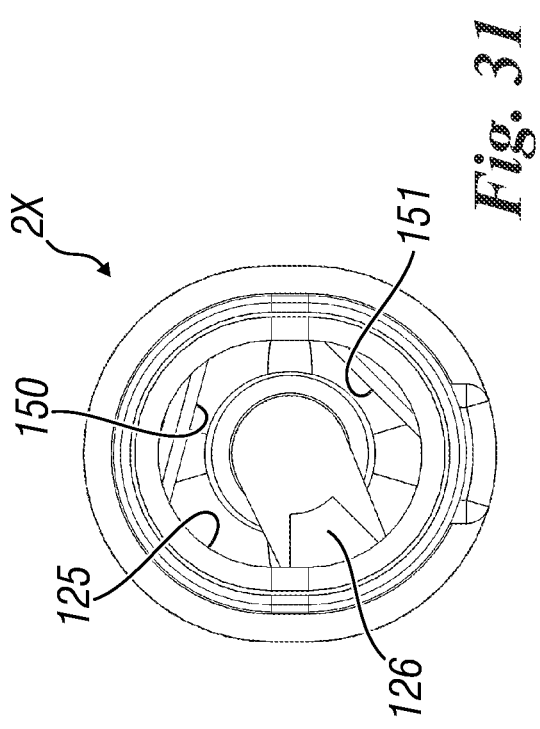

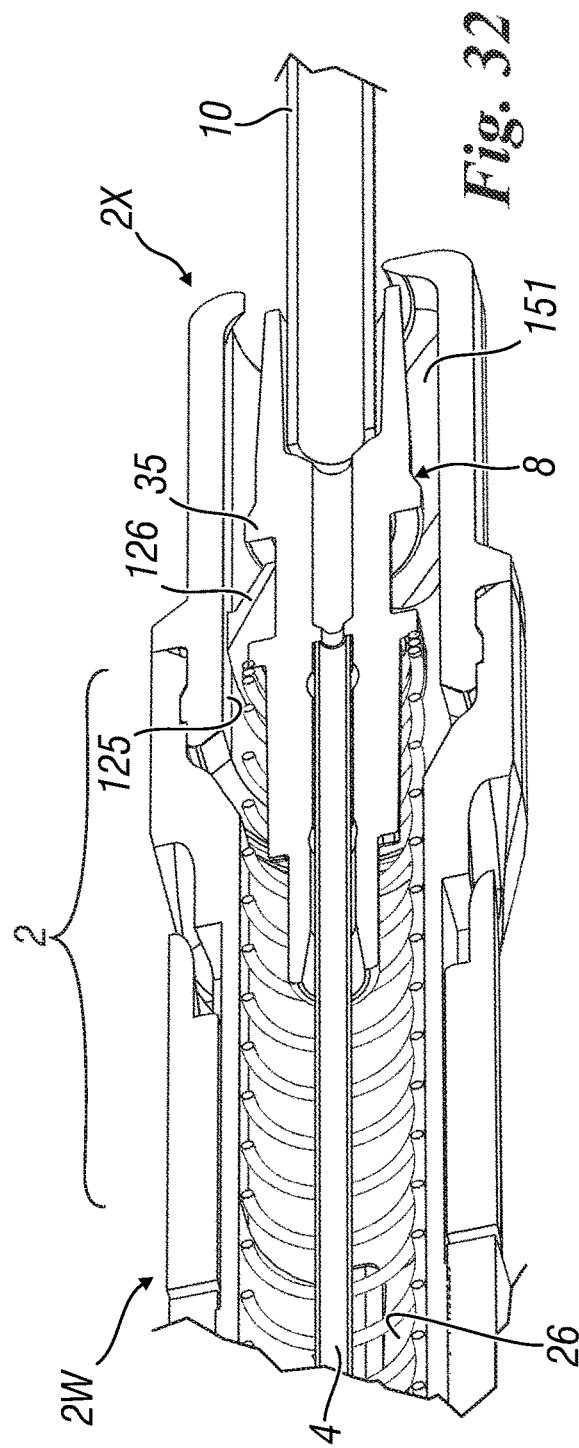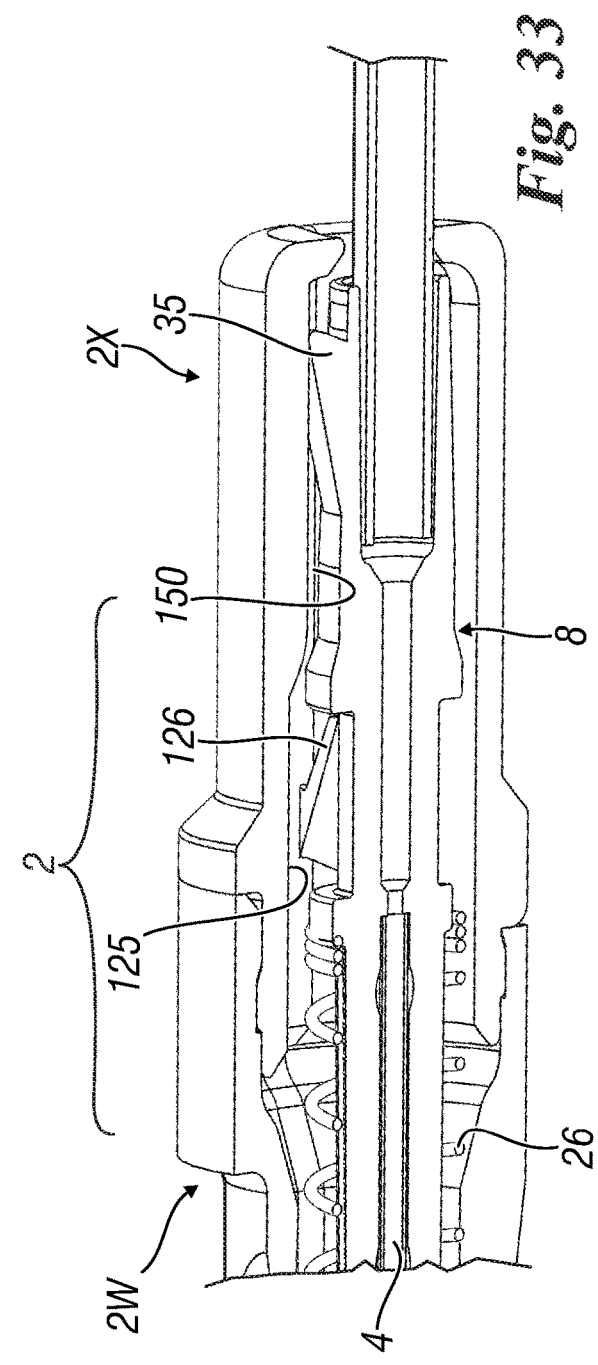

MEDICAL DEVICE WITH RESILIENTLY RETRACTING SAFETY NEEDLE

CROSS-REFERENCE TO RELATED APPLICATIONS

This application is a 371 of PCT/IB2018/056808, filed Sep. 6, 2018, which claims the benefit of Italian Patent Application No. 102017000103120, filed Sep. 14, 2017.

FIELD OF THE INVENTION

The present invention relates to a medical device according to the precharacterising clause of claim 1.

BACKGROUND OF THE INVENTION

Many medical devices for percutaneous or venous access for administering fluids to a patient or withdrawing them from one are known. Examples of these medical devices are micro infusion needles, fistula needles and catheter needles.

Medical devices of this type comprise a rigid component having a free cutting end, usually a metal cannula, attached to a first end of a cannula holder. The latter is inserted into a body of the device and has a second end to which a (plastics) tube is attached, through which the fluid administered to the patient or drawn therefrom flows. The tube (and a connector connected to it) allows body fluids to be transferred to and from suitable accessories, for example, test tubes for sampling under vacuum.

The cannula passes through the patient's skin and places the other components of the device, which are usually of plastics, in fluid communication with the sampling or infusion site.

In some of these devices, for example, in fistula and micro infusion needles, there are very flexible plastics components (such as soft plastics wings) which help the cannula to be properly and easily inserted into the injection site. Normally the flexible wings are associated with the body of the device and can be joined together in a vertical position to aid insertion of the cannula into the patient.

Wings are also provided with a specific surface finish which makes it easier for them to be gripped, and improves the ability of the skin to transpire when these wings, which are wider than the cannula, are attached to the patient by means of suitable removable attachment elements.

With these devices there is the problem associated with possible contact between the cannula (cutting at the tip) and a health operator after the device has been used in the patient. This may give rise to the transmission of infectious diseases, including very serious and debilitating ones, such as, for example, AIDS and types of viral hepatitis. For this reason, medical devices of the above-mentioned type provided with safety systems to prevent accidental punctures are known.

For example, the use of a tubular protective body in sufficiently rigid plastics material which is manually moved forward over the cannula after use into an immobilising position protecting the tip of the metal cannula is known. These systems are classified as being of the active type (because they use a specific operation in addition to the normal procedure of using the device to activate the safety).

Other devices provide that movement of the plastics protection body or, vice versa, retraction of the cannula is brought about by a suitable automatic system which can deliberately be activated by the user. Often these systems use a preloaded resilient element such as a resilient compression or tension spring as a motor for the movement.

One such device provided with a safety system is described in EP1306097. This known solution provides for a projecting flexible arm on the cannula holder which emerges from an opening in the body of the device when the latter is in a position in which the cannula is inserted into the patient's body. This arm has one end close to the cannula holder in the form of a step which bears against an edge of the opening of the body of the device.

The cannula holder experiences the thrust of a compression spring that tends to move the cannula holder into the body of the device. This movement is however impeded by the joint action of the step end of the above-mentioned projecting flexible arm so that, as a result of suitably shaped means, it is pressed in a direction at right angles to the axis of the cannula towards the interior or said aperture. In this case the step end is pressed into the body of the device, separating itself from the edge of the opening, thus enabling the spring to displace the cannula holder within the body of the device with consequent total re-entry of the cannula within said body.

A similar solution is described in WO2016007438.

Although offering protection for the health operator using the medical device, these known solutions have a disadvantage linked to the fact that re-entry of the cannula into the body of the device can be activated in an undesired and accidental way, and this can give rise to obvious problems when the cannula is being introduced into the patient's body or at any other time when this action is unintentional.

SUMMARY OF THE INVENTION

The object of the present invention is to provide a medical device with a resiliently retracting safety needle that is improved in comparison with corresponding known solutions.

In particular, the object of the invention is to provide a medical device of the type indicated which is easy and safe to use, making it possible to avoid accidental retraction of the needle during normal use.

Another object is to offer a medical device of the above-mentioned type which ensures complete and stable retraction of the cannula within the body of the device, at the same time making it impossible for it to subsequently emerge from that body and providing absolute protection against accidental contacts between such needle or cannula and a user or health operator.

Another object is that of providing a device of the type mentioned which is ergonomic and easy to hold and intuitive to use.

A further object is to provide a device of the above-mentioned type which is compact, of solid construction and free from any parts which are difficult to construct and/or which may suffer possible and likely deformation and breakage during transport or storage throughout the service life of the device.

Another object is to provide a device of the above-mentioned type which does not give rise to any problems for the patient or causes body fluids to splash during retraction during the stage when the needle or cannula is withdrawn into the body of the device.

These and other objects which will be apparent to those skilled in the art are accomplished by a medical device according to the appended claims.

BRIEF DESCRIPTION OF THE DRAWINGS

For a better understanding of the present invention the following drawings are attached merely by way of a non-limiting example, in which:

FIG. 3 shows a perspective view of a component of the device in FIG. 1;

FIG. 4 shows a cross-section along the line 4-4 in FIG. 3;

FIG. 6 shows a perspective view of another component of the device in FIG. 1 from one side;

FIG. 7 shows a cross-section along the line 7-7 in FIG. 6;

FIG. 8 shows a perspective view of another component of the device according to the invention;

FIG. 9 shows a cross-section along the line 9-9 in FIG. 8;

FIG. 10 shows a perspective view of a further component of the device according to the invention;

FIG. 11 shows a cross-section along the line 11-11 in FIG. 10;

FIGS. 15 and 16 respectively show a variant of the device according to the invention, in longitudinal cross-section, in position of use and after such use;

FIGS. 18, 19 and 20 show longitudinal cross-sectional views of different variants of the device according to the invention in the position of use;

FIG. 21 shows a perspective view of a further variant of the device according to the invention;

FIG. 22 shows a perspective view of a component of the device in FIG. 21;

FIGS. 23A and 23B show longitudinal cross-sections of the device in FIG. 21 during use with a patient and after such use respectively;

FIG. 25 shows an exploded perspective view of one component of the device in FIG. 24;

FIGS. 27 and 28 show longitudinal cross-sectional views of the device in FIG. 24 in a stage when it is ready for use with a patient and in a stage after such use, respectively;

FIG. 29 shows a longitudinal cross-section of one variant of part of the device according to the invention;

FIG. 30 shows the part in FIG. 29 in perspective view from another angle and in longitudinal cross-section;

FIG. 31 shows a cross-section along the line 31-31 in FIG. 29; and

FIGS. 32 and 33 show a perspective view and a lateral view respectively of longitudinal cross-sections of the terminal portion of the device according to the invention, where the part shown in FIG. 29 is present.

DETAILED DESCRIPTION OF THE INVENTION

Figure 1:
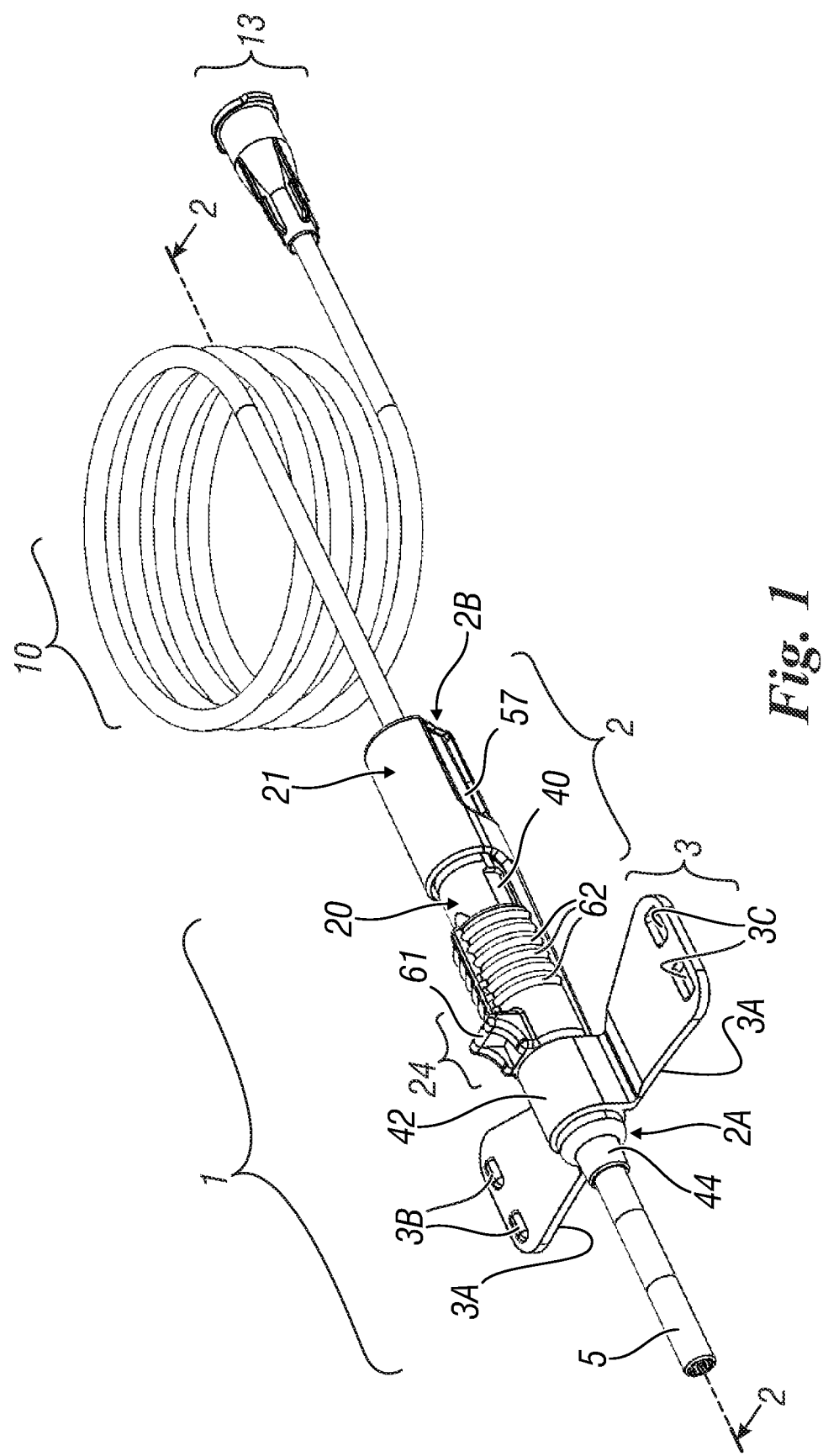
FIG. 1 shows a perspective view of a device according to the invention before it is used in a patient.
Figure 2:
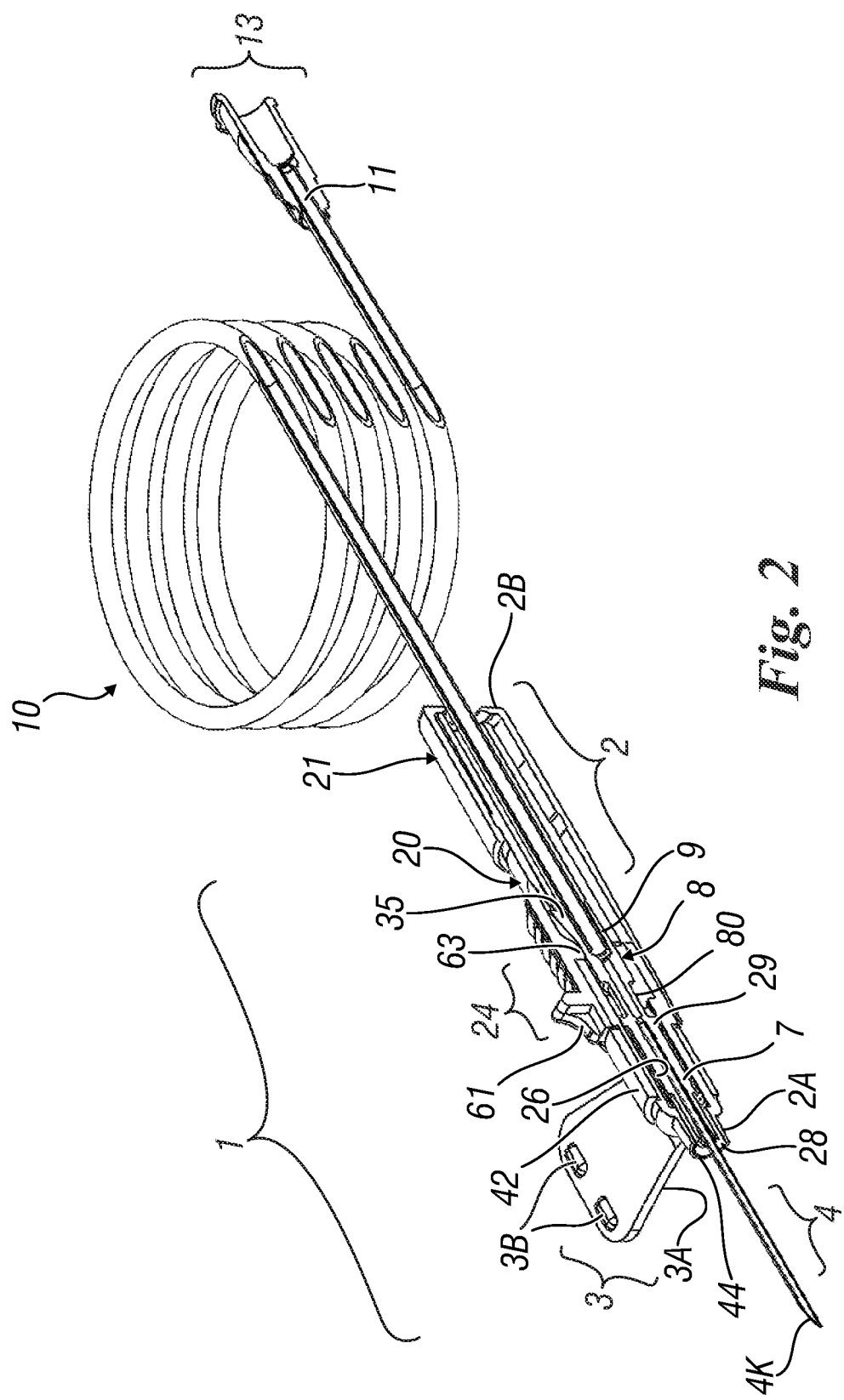
FIG. 2 shows a cross-section along the line 2-2 in FIG. 1.

With reference to the figures mentioned, a medical device according to the invention is generically indicated by 1 and comprises a tubular body 2 acting together with wings 3 (which can be separated from body 2 or are of one piece with such body) and from which there projects a cannula 4 (at a first extremity 2A thereof). When the device is not in use the latter is covered by a removable protection element 5. As will be described, cannula 4 can be retracted into body 2 after use.

In a manner which is in itself known, cannula 4 is attached to a (distal) flat end portion 7 of a cannula holder 8 (which can move in body 2 when the cannula retracts) having a second (proximal) end or end portion 9 which is of one piece with a normal tube 10. At one free end 11 of such tube 10 there is a connector 13 of the Luer Lock type, which is in itself known.

Body 2 may in a first version be of one piece and have a second end 2B, a clip-closure cover (not shown) to prevent cannula holder 8 emerging from such second end 2B when the cannula retracts into body 2. This cover may be replaced by a suitable restriction or permanent deformation in second end 2B obtained during assembly of device 1 and after cannula holder 8 has been inserted into body 2.

In the embodiment in the figures, body 2 is constructed using two sleeves 20 and 21, that is a sleeve 20 which is internal (or, better, partly internal) to an outer sleeve 21. On this body 2, and in particular internal sleeve 20 projecting from outer sleeve 21, there is a cursor 24 capable of activating the re-entry movement of cannula 4 into body 2 (in the case in the figures, into inner sleeve 20). This movement is brought about by compression spring 26 located between the first end 2A of inner sleeve 20 (from a hole 28 in which cannula 4 emerges) and a collar 29 made on first end 7 of cannula holder 8.

More particularly, wings 3 are made of soft plastics (for example, soft PVC or TPE) and can be easily folded back onto each other in a vertical position and can be easily grasped thanks to projections (not shown and in themselves known) present on an under surface 3A of the wings. The wings remain paired thanks to suitable protrusions 3B which insert into corresponding recesses 3C when the wings are vertical.

Figure 5A:
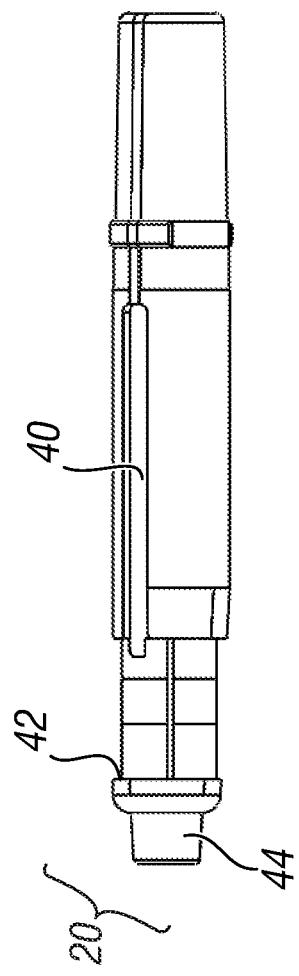
FIGS. 5A-5B and 5C show side views of variants of the component in FIG. 3.
Figure 5B:
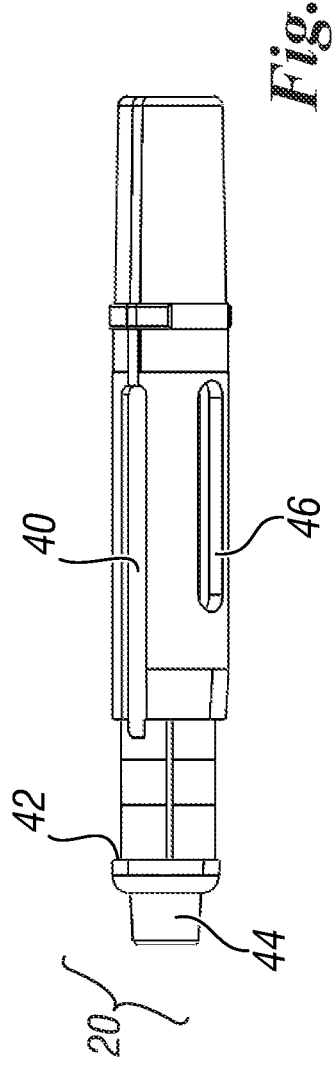
Figure 5C:
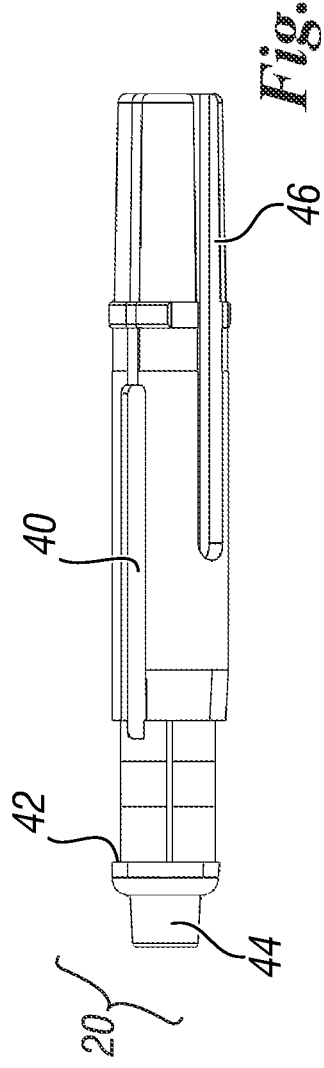
Figure 12:
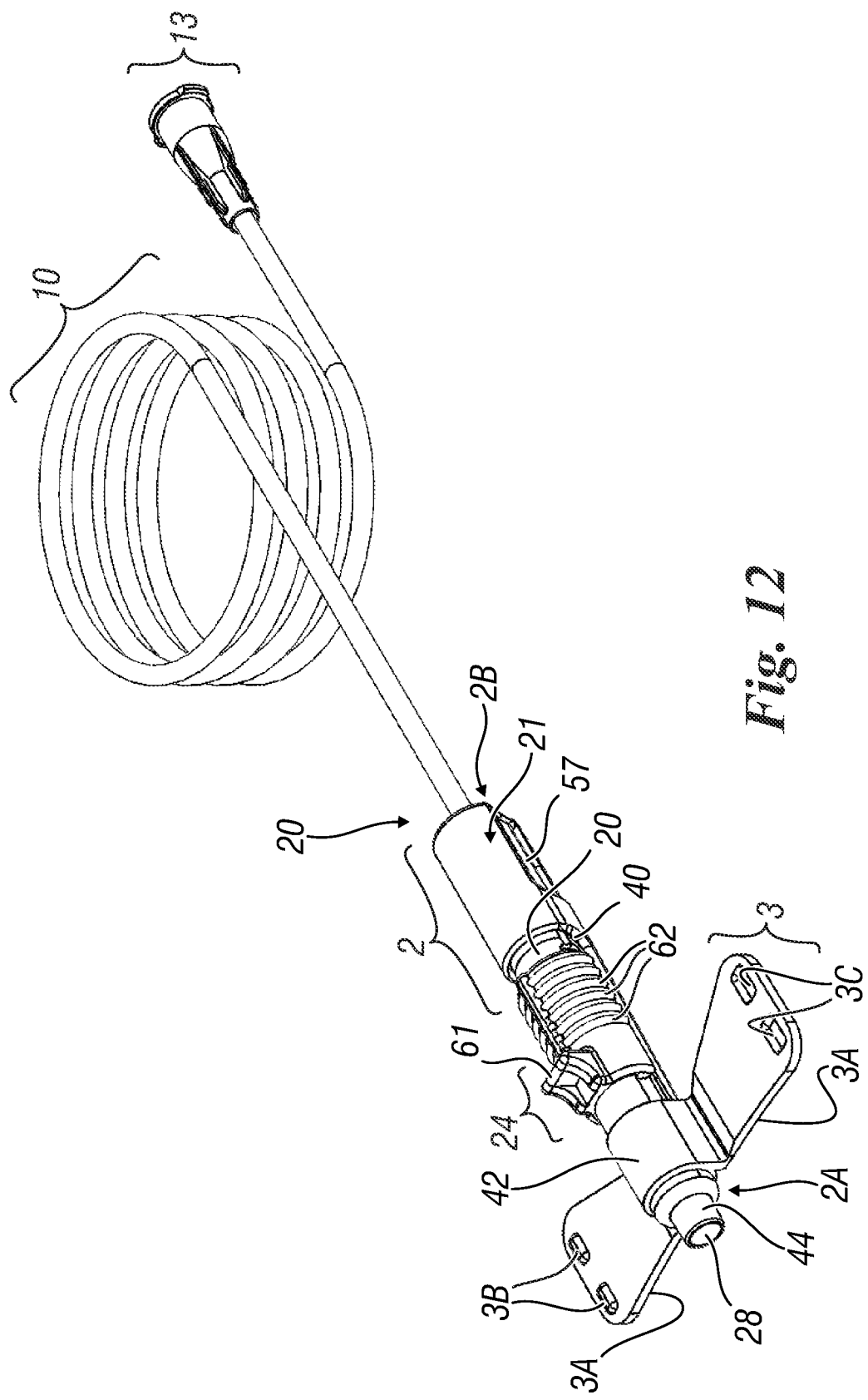
FIG. 12 shows a perspective view of the device in FIG. 1 after use.

FIGS. 3 and 4 show inner sleeve 20 which is tubular and comprises the protection for cannula 4 after it has re-entered within body 20. FIGS. 5A-5C show some possible variants of this inner sleeve.

Inner sleeve 20 is made of rigid plastics material (for example, polycarbonate) and may also be transparent. Inner sleeve 20 has an inner guide 30, preferably of variable cross-section, close to first end 2A of that sleeve. Guide 30 enables cannula holder 8 to retract in a guided manner above all during the initial stage of the movement. Inner sleeve 20 also has a window 31 having a side 32 defined by an inclined plane. This inclined side or plane 32 (acting as a member stopping the cannula holder) projects into window or cavity 31 and interferes with an immobilising tooth 35 of cannula holder 8, as will be described. As may be seen from FIGS. 4, 10 and 11, inclined plane or side 32 and the immobilising tooth act together alternately to impede or allow activation and retraction of cannula holder 8 following movement of cursor 24.

Inner sleeve 20 has a channel 36 close to second end 2B (coinciding with that of body 2) which with guide 30 enables cannula holder 8 to move back in line and prevents it from rotating. In addition to this, sleeve 20 has lateral guides 40 housing suitable projections 30 of cursor 24 and guiding them along body 2 and a shaped frontal recess 41 to house a coupling member 42 for soft plastics wings 4 in an orientated manner.

Finally, inner sleeve 20 has a cylindrical frontal projection 44 capable of housing protected element 5 of cannula 4 and ensuring that tip 4K of the cannula is covered after the mechanism for withdrawal into body 2 (or the safety mechanism) has been activated with consequent re-entry of the cannula into body 2, said return mechanism incorporating spring 26.

Another groove 46 is provided in the embodiments in FIGS. 4, 5B and 5C and facilitates assembly of the cannula holder within sleeve 20.

Inner sleeve 20 also comprises a portion 47 of cavity 34 which is of wider cross-section than the remaining part of aforesaid cavity 34. In addition to this, on the outside, inner sleeve 20 has an outer flange or collar 49 and second end 2B is preferably of oval cross-section to ensure correctly orientated assembly with outer sleeve 21. The oval section can increase the ergonomics of the device by aiding a secure and correctly orientated grip on the body of the device in comparison with a cylindrical cross-section.

FIGS. 6 and 7 show outer jacket 21 comprising a tubular terminal portion 54 from which a lower extension 55 capable of closing off groove 46 of inner sleeve 20 projects. A hole 56 is provided in terminal portion 54 for the passage of tube 10, and shaped lateral holes 57 (as in portion 54) or shaped elements are provided on the sides of portion 54 itself in order to assist grip on device 1.

Sleeves 20 and 21 are coupled together and nested through the insertion of outer collar 49 of sleeve 20 into an annular recess 58 provided internally in terminal portion 54 of outer sleeve 21. This coupling may alternatively be constructed or strengthened using welding (for example, thermal or ultrasound welding) or by means of adhesive bonding, or any other known system.

FIGS. 8 and 9 show activation cursor 24 for the "retraction mechanism" for cannula 4 in body 2 (that is, in the example, into inner sleeve 20). This mechanism comprises spring 26 and cannula holder 8 which because of its shape (as will be described) and acting together with said cursor 24, can take up a displaced position with respect to first end 2A of body 2 (or inner sleeve 20) or towards second end 2B of such body. In the latter position cannula 4 is within the body and protected from accidental contacts.

As illustrated, one possible configuration of the cursor comprises a hemicylindrical (or substantially hemicylindrical) body 60 which can be positioned and move along inner sleeve 20. This body 60 has externally a shaped projection 61 capable of receiving the finger of an operator using device 1 and surface ribs 62 enabling the operator to have a direct grip on the cursor.

Internally there is a protuberance 63 having an inclined wall 65 which is capable of acting together with immobilising tooth 35 of cannula holder 8. This joint action results in initial relative movement of cursor 24 over said tooth 35 without any immediate consequent movement of cannula holder 8 in sleeve 20. It will be noted that, as illustrated in FIGS. 10 and 11 in particular, this immobilising tooth 35 has an inclined wall 66 over which wall 65 of cursor 24 can move, cooperation between said inclined walls 66 and 65 converting the axial displacement force of the cursor on sleeve 20 into a vertical component which detaches such immobilising tooth 35 from inclined side 32 of sleeve 20 (acting as the stop member for body 2 capable of preventing movement of cannula holder 8 until it is required). As described above, before immobilising tooth is released, cursor 24 has to travel a few millimetres, which together with the joint action of the inclined planes, the materials used and the friction obtained help to reduce the risk of accidental activation (because accidental contact with the cursor would make it difficult to cause activation of the retraction mechanism), while at the same time maintaining easy and comfortable activation. It will be noted that the problem of accidental activation is frequent in known medical devices, in which it is only necessary to press the button lightly to activate retraction; some known solutions have attempted to eliminate this risk by, for example, protection devices which have to be removed in order to gain access to the button, but this has introduced additional operations for the use which are not very practical. One example of such known embodiments is described in the prior art cited in the introductory part of this text. It will be noted that activation of the retraction mechanism is very intuitive and easy, in that movement of cursor 24 takes place in the same direction in which cannula 4 is extracted from the patient's vein, reducing the difficulty perceived by the user.

FIGS. 10 and 11 show cannula holder 8 which ensures hydraulic continuity between cannula 4 and tube and enables the cannula to remain exposed until the user deliberately activates the retraction mechanism. Cannula holder 8 comprises first (distal) part 7 and second part 9 (which is proximal with respect to tube 10).

Part 9 which is proximal to the tube is characterised by a specific shape and incorporates immobilising tooth 35 enabling rigid attachment to sleeve 20. The distal part of the tube comprises a housing 69 for the cannula and surface ribs 70 (possible ribs, but these may or may not be present) capable of acting together with spring 26 to hold the spring back, but which are capable of moving without rotation within the inner sleeve.

In the embodiment illustrated in the figures, between distal part 7 and proximal part 9 there is a yielding part 80 which permits relative movement between distal part 7 and proximal part 9 of cannula holder 8. In the figures this yielding part is illustrated as a portion 80 of reduced cross-section ("thinned" or of varied cross-section) capable of ensuring deformability of cannula holder 8 and allowing rigid immobilising tooth 35 to move downwards under the action of cursor 24 within portion 47 of cavity 34 of sleeve 20. Unlike known solutions (for example, EP 1306097 and WO 2016007438), in the present invention there is no resilient arm projecting from the cannula holder, but it is a whole portion of the cannula holder which moves downwards within inner sleeve 20 so as to release rigid immobilising tooth 35 (which is non-elastic and non-resilient) under the force of cursor 24.

Yielding portion 80 may also be obtained by constructing it as an area of different cross-section from that of parts 7 and 8, through a portion obtained from a yielding material which is in itself known or in any other manner which permits relative movement between parts 7 and 9 of cannula holder 8.

In addition, and contrary to the known solutions described above, activation of the retraction mechanism does not take place through pressure in a radial direction, directly on the flexible arm, or through the interposition of a button which has to be pressed, but occurs indirectly through cursor 24 (which runs with sleeve 20).

Figure 13A:
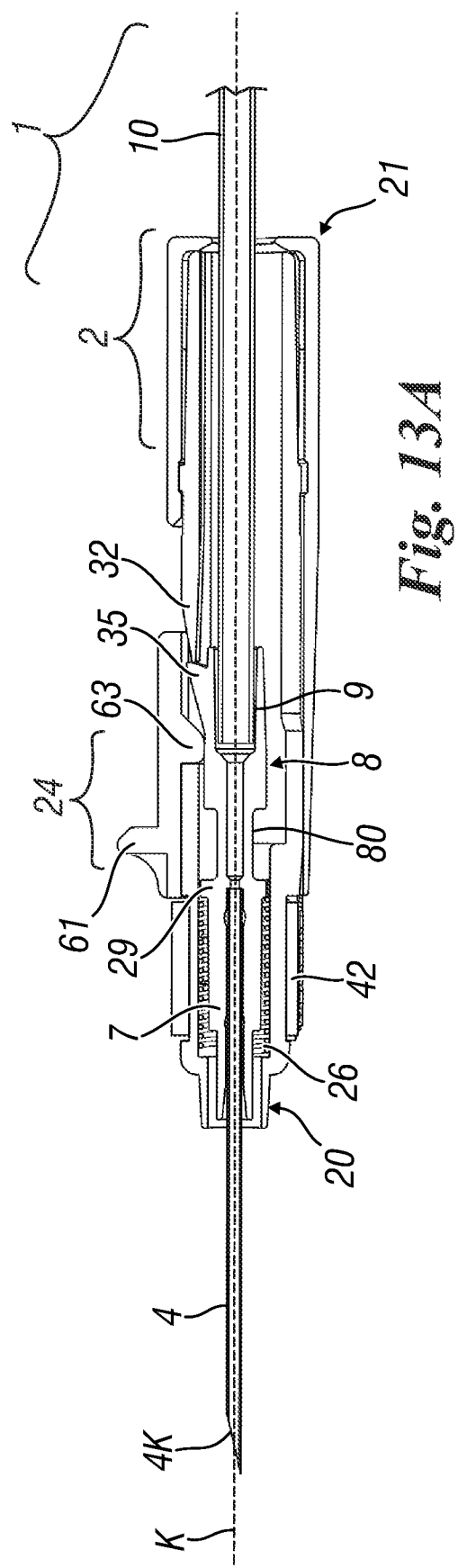
FIGS. 13A, 13B and 13C show various stages in the re-entry of a cannula of the device within the body of the latter, the device being shown in longitudinal cross-section in the various figures.

The invention is used as follows: after sterile device 1 has been removed from its container, if it is not already present, connector 13 on tube 10 is connected with a suitable accessory (which is in itself known, for example, a syringe or connector for sampling under vacuum) depending upon the medical procedure being engaged in. Wings 3 are folded, and protected element 5 is removed, preventing damage to tip 4K of cannula 4 before use. Metal cannula 4 is inserted into a vein or into another suitable site depending upon the medical procedure engaged in and the wings are released after they have been positioned on the patient's skin and taped with suitable medication to stabilise the medical device in the event of prolonged sampling/infusion. After the fluids have been administered to and/or withdrawn from the patient, and the stabilising device may have been removed, a folded bandage (or equivalent) is positioned on the injection site close to cannula 4 to prevent the release of body fluids following retraction of the cannula. The retraction mechanism is activated through moving cursor 24 axially along body 2, in a linear movement parallel to longitudinal axis K of the cannula. This brings about initial displacement of protuberance or projection 63 of cursor 24 towards inclined wall 66 of cannula holder 8 (see FIG. 13A), but this displacement of a few millimetres does not give rise to any thrust force on immobilising tooth 35 of cannula holder 8 itself and therefore such tooth does not move with respect to inclined side 32 of first sleeve 20 of body 2 of the device.

Figure 13B:
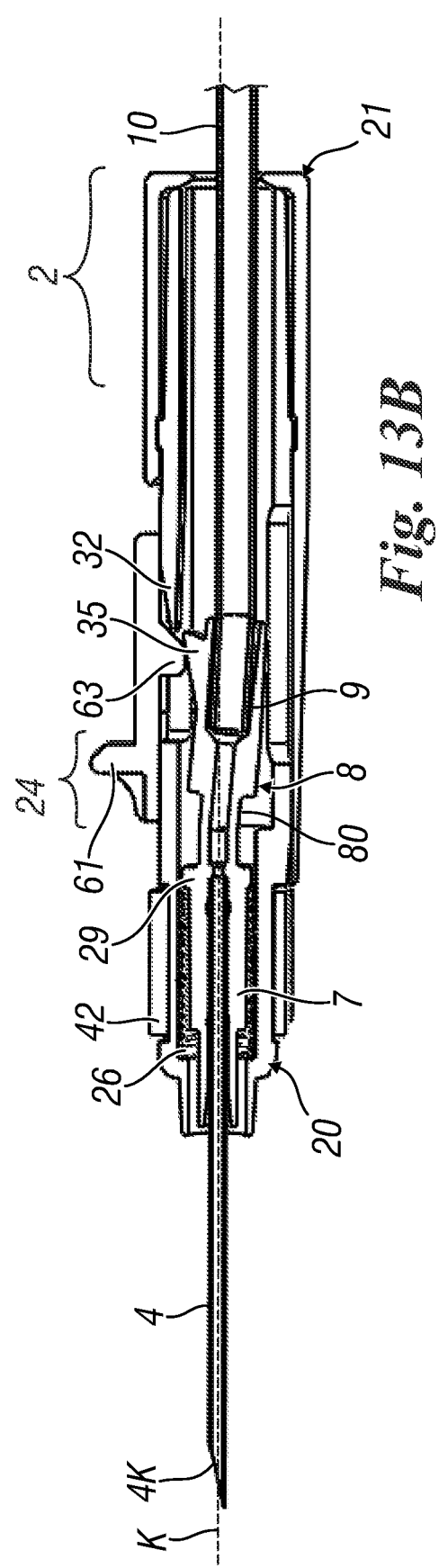

Continuing with the movement, protuberance 63 slides on wall 66 of tooth 35 and begins to press that tooth and distal portion 9 of cannula holder 8. This movement of the cursor then causes cannula holder 8 to bend in its portion of reduced or different cross-section 80 (as previously described) (which acts as a "hinge" between distal portion 7 and proximal portion 8 of the cannula holder), bending which causes immobilising tooth 35 to detach from inclined side 32 (see FIG. 13B).

Figure 13C:
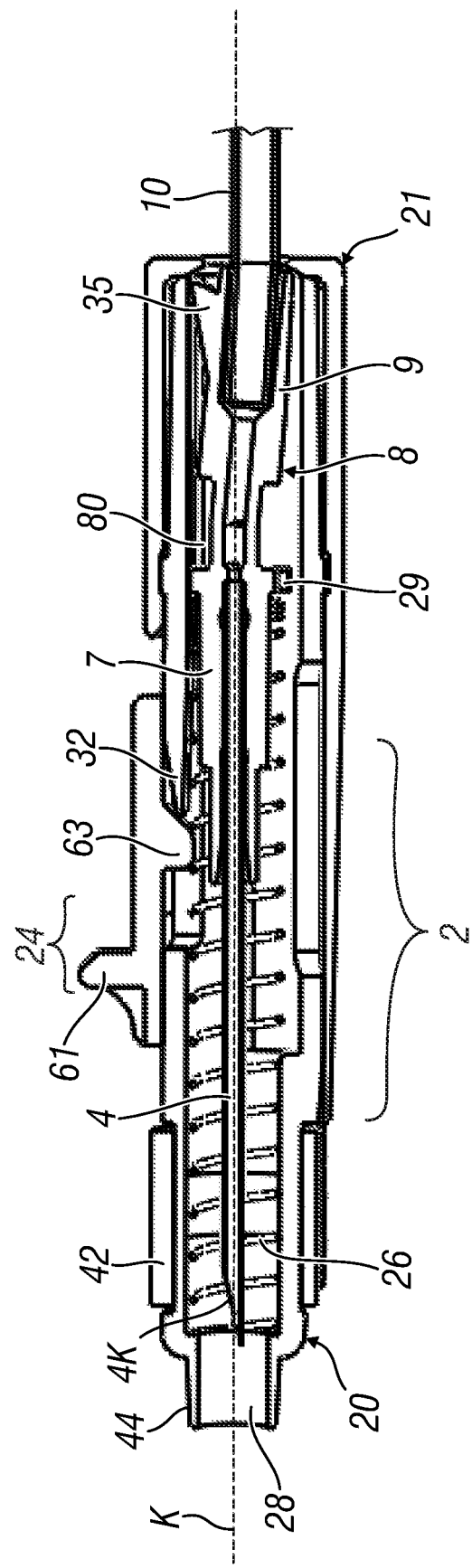
Figure 14:
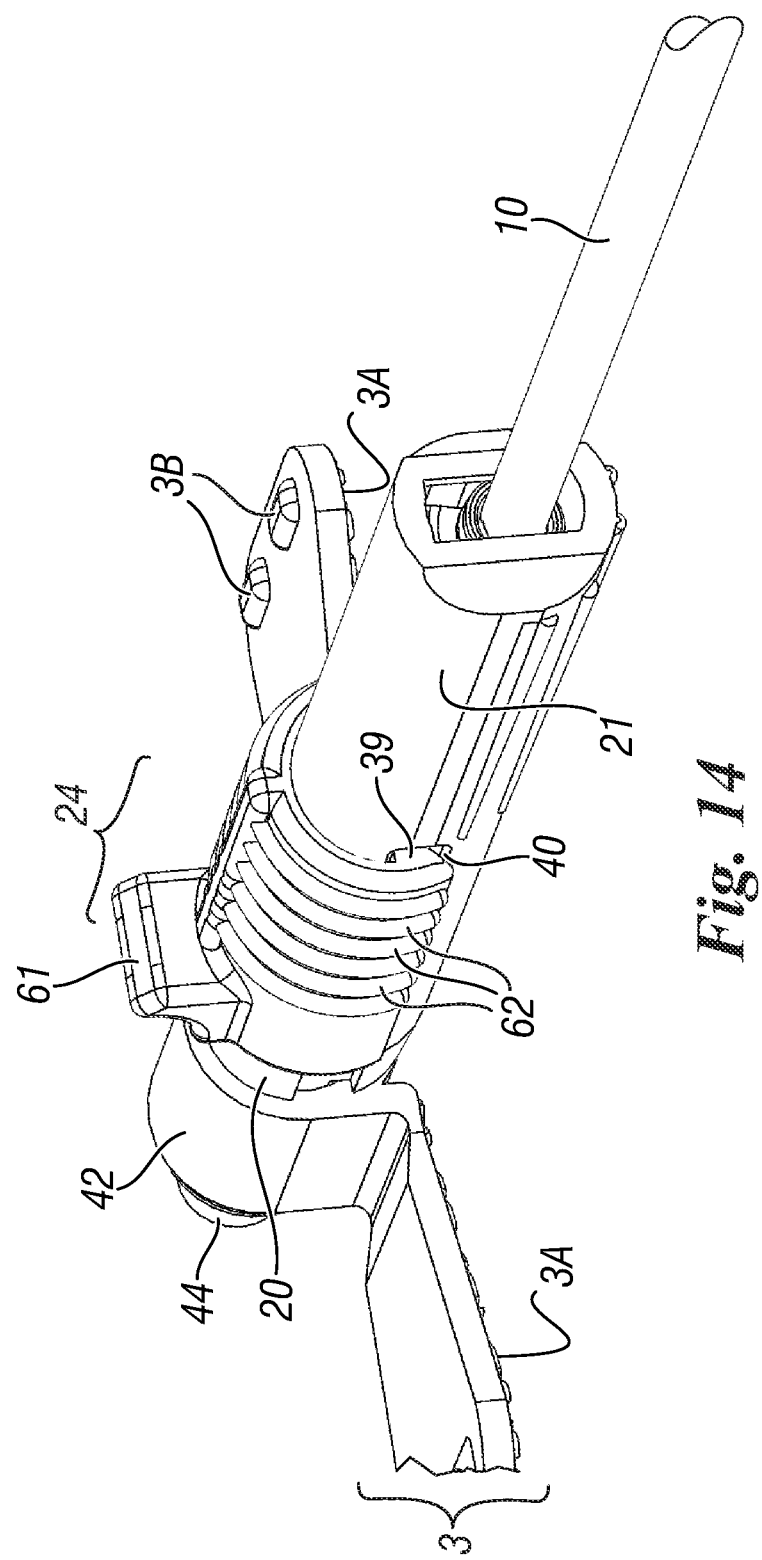
FIG. 14 shows a perspective view of the device in FIG. 1 from one side.
Figure 17:
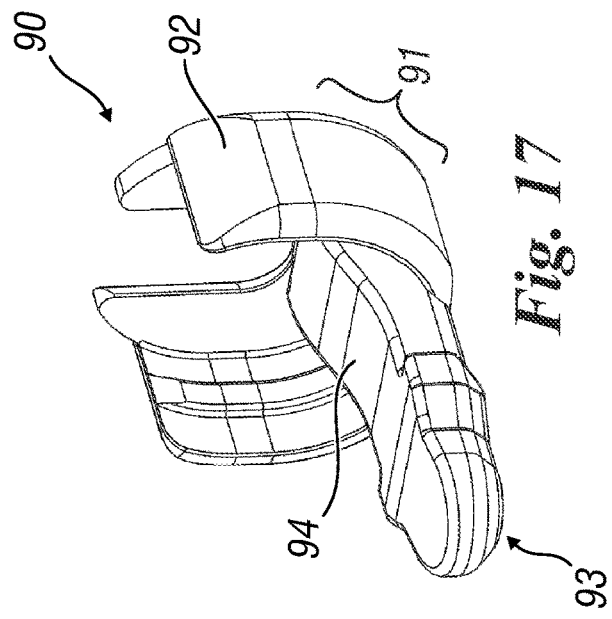
FIG. 17 shows a perspective view of one component of the variant of the device in FIGS. 15 and 16.

At this point, as there is no stop to the movement of cannula holder 8, spring 26 presses such cannula holder 8 towards end 2B of body 2 causing tip 4K of cannula 4 to retract and disappear into body 2 of the device. Furthermore (see FIG. 14), cannula holder 8 is completely within body 2 (see FIG. 13C).

Thanks to groove 36, proximal portion 9 of the cannula holder is displaced from the K axis, stably folding itself within body 2.

It is known that, as usual, spring 26 has the task of storing the resilient energy necessary for generating a force which when released through deliberate activation is such that it fully retracts cannula 4 into inner sleeve 20. However, spring 4 does not extend completely as a result of activation and therefore helps to hold cannula holder 8 within inner sleeve 20 and prevent the tip 4K of the cannula from being exposed following accidental impacts which, in the invention described here, can only act on the tube, which being flexible can compensate for the effects of the impact without generating translational movement of the cannula holder. In the known solutions mentioned above (EP 1306097 and WO 2016007438) the rigid cannula holder projects from the rear of the body of the device after activation and it is therefore necessary to use resilient immobilising means to prevent the cannula from again being exposed following accidental impacts which might act on this rigid part which is inherently unable to compensate for any deformation.

FIGS. 15 and 16 show a variant of the invention in which body 2 has a closure element 90 for end 2B; said element comprises a body 91 with an open annular portion 92 which engages end 2B of body 2 and with a projecting portion 93 having a part 94 capable of coming into contact with cannula holder 8 when retracted into body 2 of the device. This part 94 is wedge-shaped so as to move proximal end 9 of the cannula holder in a direction at right angles to it. This causes immobilising tooth 35 to project from an opening 97 made in end 2B of body 2 when cannula holder 8 reaches the end of its travel. This provides evidence that cannula 4 has safely re-entered body 2, that is, the retraction mechanism of device 1 has been correctly activated.

In this position, the cannula holder can no longer be made to enter body 2.

Figure 18:
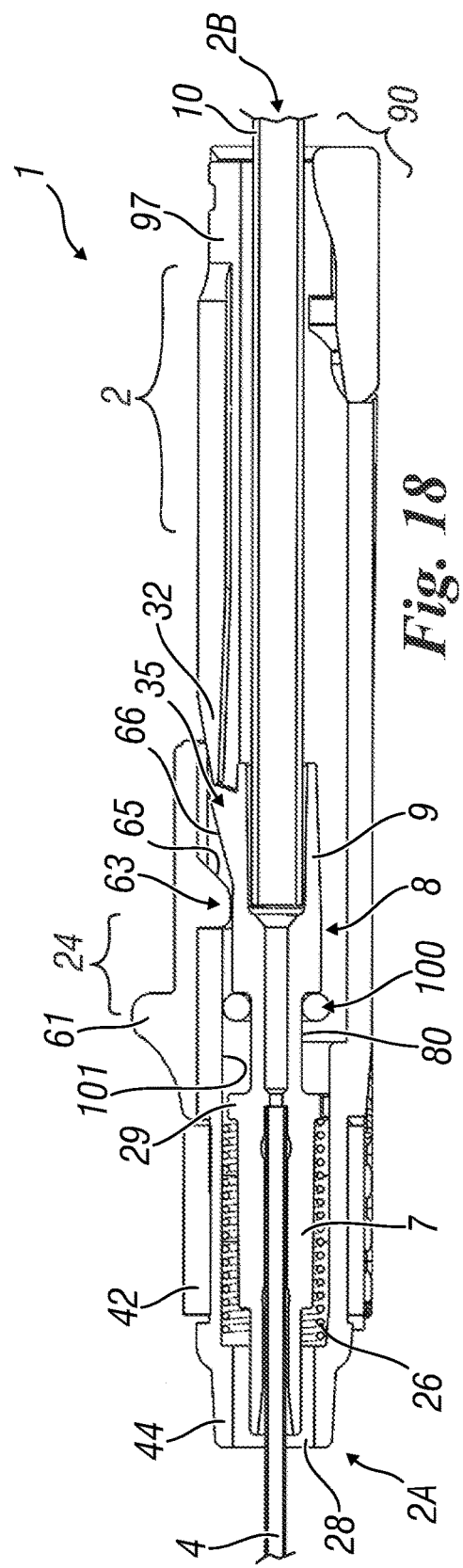
Figure 24:
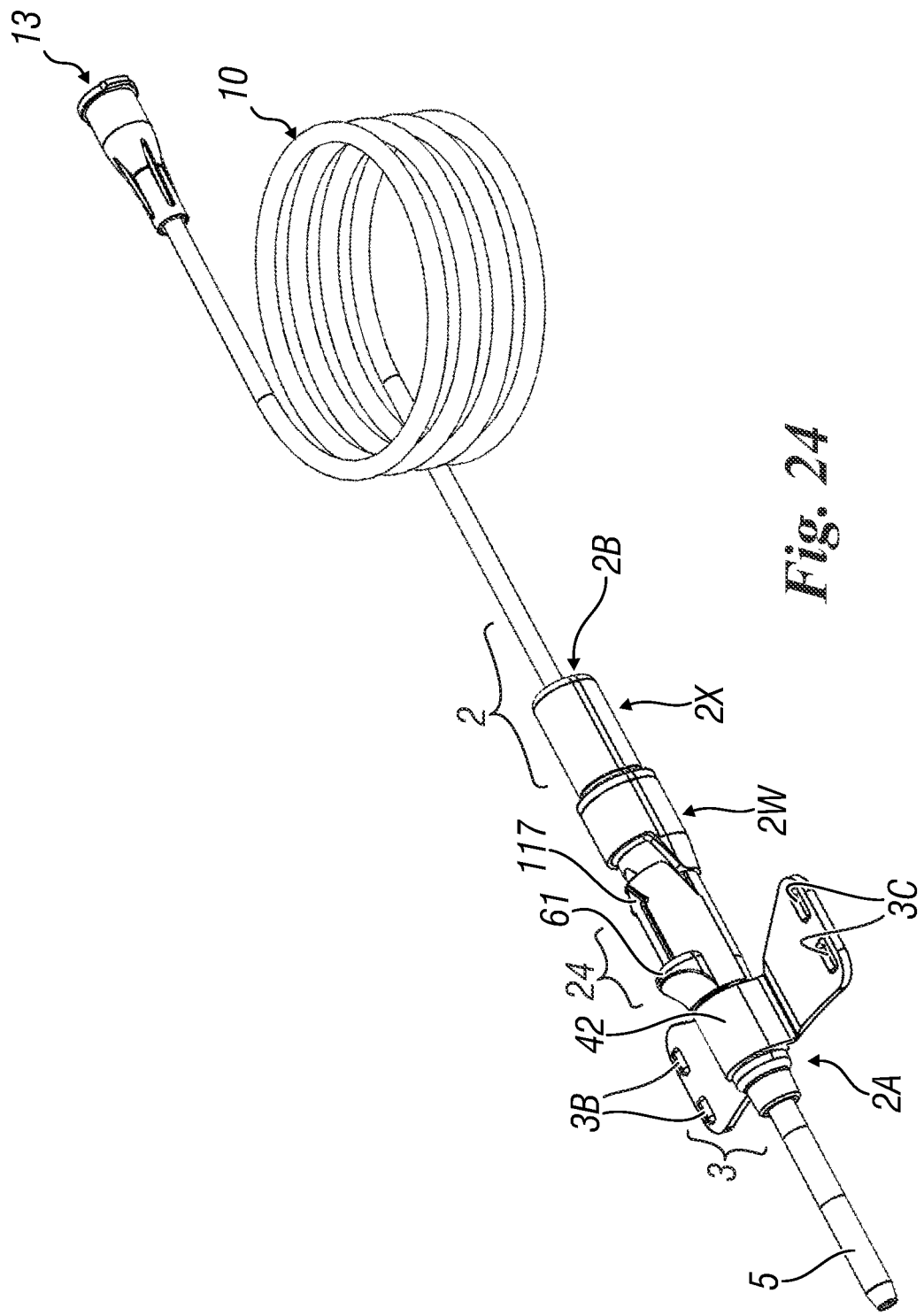
FIG. 24 shows a perspective view of a further embodiment of a device according to the invention.
Figure 26:
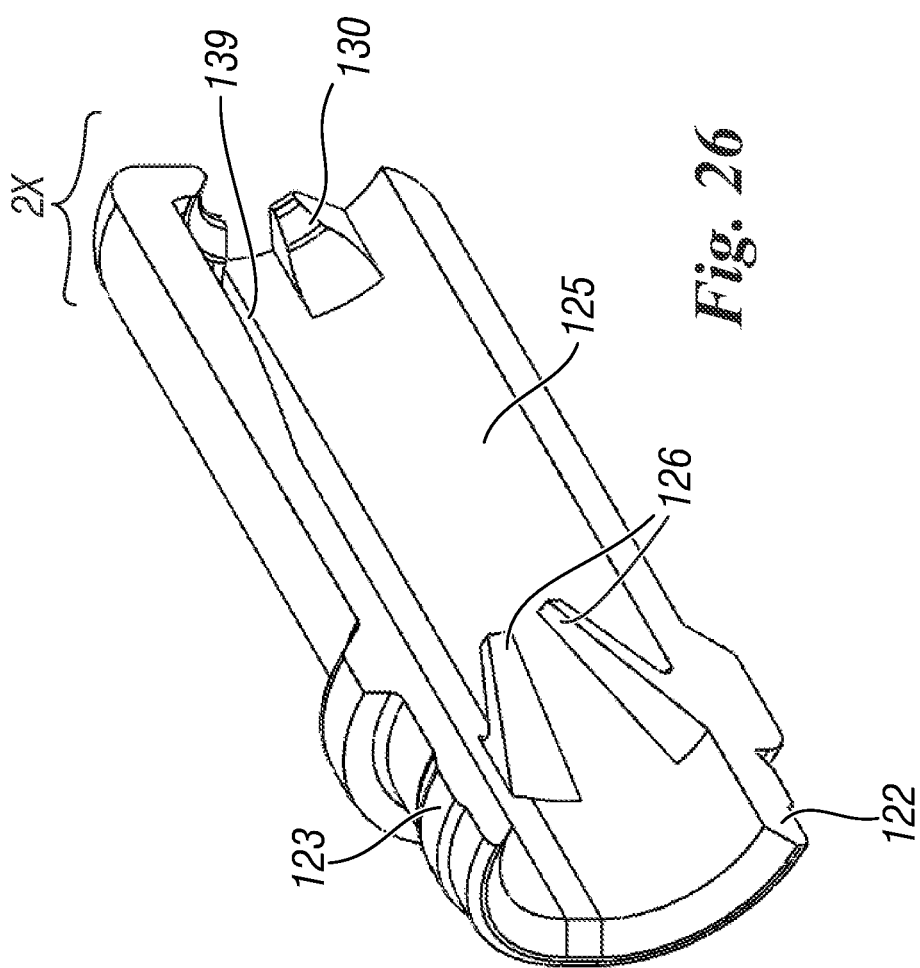
FIG. 26 shows a cross-section along the line 26-26 in FIG. 25.

In FIGS. 18-20, device 1 (always connected to a tube 10 which is inherently not part of the inventive device) provides for the use of braking members 100 associated with cannula holder 8 in FIG. 18, an elastomer ring being inserted into portion 80 of reduced cross-section of the cannula holder. During retraction this ring touches inner wall 101 of sleeve 20, slowing the movement of cannula holder 8.

In FIG. 19, the elastomer ring is replaced by a foam ring (made of or soaked with a material or substance having high viscosity/viscoelasticity such as, for example, high viscosity silicone grease); in FIG. 20, this ring is replaced by braking wings of deformable plastics material. The action of the wings in combination with wall 101 provides a braking effect, this effect being greater at the start of the cannula holder's movement when the wings deform against wall 101 of sleeve 20 following movement of proximal end 9 of cannula holder 8 pushed by cursor 24 into such sleeve.

FIGS. 21-23B show a further variant of the invention in which closure element 90 has a portion 93 constructed in a resiliently deformable manner: this portion comprises a tongue 110 which is inclined with respect to a base 111 and rises from such base with an end 112. The resilient tongue presses proximal portion 9 of cannula holder 8 towards opening 97 in such a way that the immobilising tooth (which may be coloured) can emerge from it.

In addition, cursor 24 has an indicator 117 of the direction of translational movement on body 2.

FIGS. 24-28 illustrate a further variant of the invention.

In the figures, device 1 is optimised for automatic or semi-manual assembly; such a device comprises body 2 divided into two portion 2W and 2X so as to make cannula holder 8 more accessible for assembly tools (such as, for example, shaped supports). The two portions of the body 2W and 2X are lined up and assembled axially using, for example, a snap joint. This joint is defined by one end 120 of first part 2W (or distal portion of body 2) having at least one recess 121 capable of receiving an end 122 of the second part (or proximal portion of body 2 with reference to tube 10) having a collar 123 capable of making a snap connection with such recess 121 in order to make the joint between parts 2W and 2X.

Proximal portion 2X of body 2 (of tubular shape, like distal portion 2W) has an inner wall 125 from which project one or more resilient arms 126 capable of acting together with portion 80 of the cannula holder when the latter is retracted within body 2 of the device in order to prevent movement towards first end 2A of such body. The resilient arms are inclined with respect to wall 125 and face second end 2B of body 2 and their immobilising effect can be increased through the presence of an opposing inclined plane 139 which displaces cannula holder 9 towards arms 126.

If present, arms 126 also act as a brake on movement of cannula holder 8 when the mechanism for retracting cannula 4 in body 2 is activated.

Finally, proximal portion 2X has projections 130 projecting from wall 125 at end 2B of body 2 to block retraction movement of the catheter holder under the thrust of spring 26.

FIGS. 29-33 illustrate a further variant of the invention. This variant is similar to that in FIGS. 24 and 29 and therein part 2X comprises a resilient arm 126 projecting from inner wall 125 substantially opposite to inclined planes 150 and 151 again located on that inner part 125. Arm 126 always acts as a member immobilising the cannula holder when it is completely retracted within body 2 and acts together with inclined planes 150 and 151 (rigid undeformable elements) to retain cannula holder 8 in an immobilised position when it is in the completely retracted position. The cooperation between said arm 126 and inclined planes 150 and 151 maximises the immobilising effect of resilient arm 126.

Various embodiments of the invention have been described. Yet others are possible in order to obtain a medical device falling within the scope of the invention defined by the following claims.

The invention claimed is:

1. A medical device for percutaneous or venous access for administering a fluid to a patient or sampling from a patient, comprising:
a tubular body from which there projects a cannula supported at a distal end of a cannula holder, a proximal end of said cannula holder being attached to a tube in which said fluid can circulate, said cannula holder being able to move within said body of the medical device under a force of a resilient thrust element,
a stop member of one piece with said body and able to impede said movement of the cannula holder being provided and activating means being provided to allow said movement associated with the body of the medical device acting together with activating counter-means of one piece with said cannula holder,
wherein said cannula holder has a yielding part positioned between and coaxially joined to its said distal end and to said proximal end whereby said yielding part is in fluid communication with said distal end and with said proximal end, said yielding part being configured to allow said cannula holder, at the proximal end, to flex within the body of the medical device when said activating means are activated so as to separate said cannula holder from said stop member to allow axial movement of the cannula holder in the body of the medical device and disappearing retraction of the cannula into the body.

2. The medical device according to claim 1, wherein said yielding part is obtained alternatively by means of a reduced portion or section of the cannula holder, a portion made of yielding material or a portion having a cross-section which is different from that of the distal end and the proximal end of said cannula holder, flexion of the cannula holder being of an axial type or about its own longitudinal axis.

3. The medical, device according to claim 1, wherein the activating means comprise a cursor moving in translation in a guided way along the body of the medical device and comprising a projection projecting within an internal cavity of the body through a window provided in said body, said projection acting together with a rigid immobilising projection or tooth of one piece with the cannula holder defining the activating counter-means.

4. The medical device according to claim 3, wherein said projection of the cursor comprises an inclined wall configured to act together with a corresponding inclined wall of the rigid immobilizing projection or tooth when said cursor allows the cannula to move back into the body of the medical device, a combined action of said inclined walls generating a direct force towards an interior of the body of the medical device which presses on the proximal end of the cannula holder in such a way as to displace said rigid immobilising projection or tooth into a wider portion of the internal cavity of said body and cause displacement of the proximal end with respect to the distal end thanks to flexion of the yielding part and allowing the cannula holder to move into the body of the medical device.

5. The medical device according to claim 3, wherein the stop member stopping the movement of the cannula holder is an inclined side of said window made in the body of the medical device, said inclined side projecting into the internal cavity of said body and acting together with the rigid immobilising projection or tooth to impede said movement of the cannula holder into the body of the medical device while said device is being used on the patient.

6. The medical device according to claim 3, wherein said cursor can move freely over the body of the medical device before acting together with the cannula holder through the projection.

7. The medical device according to claim 1, wherein said body of the medical device comprises an internal guide with which the cannula holder acts when it retracts into said body, the movement of said catheter holder being guided along said internal guide.

8. The medical device according to claim 1, wherein the body comprises two sleeves, the two sleeves comprising an inner sleeve being partly within an other sleeve, the inner sleeve containing the cannula holder while the medical device is in use, and a cursor moving in a guided way on the inner sleeve, the cannula emerging from the inner sleeve when in use, the tube emerging from the outer sleeve, at least one of the two sleeves having openings or being shaped to aid in handling of the medical device.

9. The medical device according to claim 1, wherein said body alternatively has one end from which emerges the tube which is of reduced and deformed cross-section or which supports a closure element, this making possible to prevent the cannula holder from emerging from said body when the cannula re-enters the body itself.

10. The medical, device according to claim 1, wherein the resilient thrust element which brings about movement of the cannula holder does not reach maximum extension when the cannula is completely retracted within the body of the medical device, said resilient dement acting between the cannula holder and said body of the medical device.

11. The medical device according to claim 1, wherein braking means associated with said cannula holder or said body of the medical device are provided to slow the movement of the cannula holder in said body.

12. The medical device according to claim 11, wherein said braking means are alternatively an elastomer ring, a foam ring made of or soaked with a high viscosity/viscoelasticity material or substance or projecting wings, said braking means being associated with the cannula holder and acting together with an internal wall of the body of the medical device.

13. The medical device according to claim 11, wherein said braking means are a resilient arm projecting from an inner wall of the body of the medical device and facing an end of the body from which the tube emerges, said resilient arm also acting as an immobiliser for the cannula holder at the end of movement of the cannula holder in the body.

14. The medical device according to claim 13, wherein said body of the medical device comprises internal portions having a rigid inclined plane capable of acting together with said resilient arm in order to immobilise said cannula holder within said body at the end of its movement within the body.

15. The medical device according to claim 1, further comprising means for flexion of a proximal extremity of the cannula holder when the cannula holder is in a position in which the cannula is fully retracted within the body of the medical device, said means for flexion being—optionally located at a second end of said body from which said tube emerges, said means for flexion being advantageously coupled to said body and comprising a portion inclined towards an interior of said body in such a way as to displace the cannula holder towards an immobilising direction opposite said portion.

16. The medical device according to claim 15, wherein the body of the medical device has an opening configured to receive the activating counter-means of one piece with the cannula holder at the end of the movement of the cannula holder in the body, said counter-means projecting from the body, the counter-means being advantageously coloured.

* * * * *